(12) United States Patent
Khalil et al.

(10) Patent No.: US 10,548,727 B2
(45) Date of Patent: *Feb. 4, 2020

(54) SYSTEMS FOR PLACING A COAPTING MEMBER BETWEEN VALVULAR LEAFLETS

(71) Applicant: Edwards Lifesciences Corporation, Irvine, CA (US)

(72) Inventors: Vivian Khalil, Newport Beach, CA (US); Erin M. Spinner, Newport Beach, CA (US); Neil S. Zimmerman, Menlo Park, CA (US); Alexander J. Siegel, Costa Mesa, CA (US); Son V. Nguyen, Irvine, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 351 days.

This patent is subject to a terminal disclaimer.

(21) Appl. No.: 15/486,122

(22) Filed: Apr. 12, 2017

(65) Prior Publication Data
US 2017/0216028 A1 Aug. 3, 2017

Related U.S. Application Data

(63) Continuation of application No. 13/895,611, filed on May 16, 2013, now Pat. No. 9,636,223.
(Continued)

(51) Int. Cl.
*A61F 2/24* (2006.01)

(52) U.S. Cl.
CPC ............ *A61F 2/2427* (2013.01); *A61F 2/246* (2013.01); *A61F 2/2433* (2013.01); *A61F 2/2454* (2013.01); *A61F 2/2463* (2013.01); *A61F 2/2466* (2013.01); *A61F 2/2424* (2013.01); *A61F 2210/0014* (2013.01);
(Continued)

(58) Field of Classification Search
CPC .... A61F 2/2427; A61F 2/2433; A61F 2/2436; A61F 2/2439; A61F 2/246; A61F 2/2466; A61F 2/2425
See application file for complete search history.

(56) References Cited

U.S. PATENT DOCUMENTS

| 6,629,534 B1 | 10/2003 | St. Goar et al. |
| 6,764,510 B2 | 7/2004 | Vidlund et al. |

(Continued)

*Primary Examiner* — Kathleen S Holwerda
(74) *Attorney, Agent, or Firm* — Guy Cumberbatch

(57) ABSTRACT

The present invention relates to devices and methods for improving the function of a defective heart valve, and particularly for reducing regurgitation through an atrioventricular heart valve—i.e., the mitral valve and the tricuspid valve. For a tricuspid repair, the device includes an anchor deployed in the tissue of the right ventricle, in an orifice opening to the right atrium, or anchored to the tricuspid valve. A flexible anchor rail connects to the anchor and a coaptation element on a catheter rides over the anchor rail. The catheter attaches to the proximal end of the coaptation element, and a locking mechanism fixes the position of the coaptation element relative to the anchor rail. Finally, there is a proximal anchoring feature to fix the proximal end of the coaptation catheter subcutaneously adjacent the subclavian vein. The coaptation element includes an inert covering and helps reduce regurgitation through contact with the valve leaflets.

18 Claims, 23 Drawing Sheets

Related U.S. Application Data

(60) Provisional application No. 61/734,728, filed on Dec. 7, 2012, provisional application No. 61/647,973, filed on May 16, 2012.

(52) U.S. Cl.
CPC .......... *A61F 2210/0061* (2013.01); *A61F 2230/0023* (2013.01); *A61F 2250/001* (2013.01); *A61F 2250/0003* (2013.01)

(56) References Cited

U.S. PATENT DOCUMENTS

| | | | |
|---|---|---|---|
| 7,160,322 B2 | 1/2007 | Gabbay | |
| 7,404,824 B1 | 7/2008 | Webler et al. | |
| 7,556,646 B2 | 7/2009 | Yang et al. | |
| 7,678,145 B2 | 3/2010 | Vidlund et al. | |
| 7,785,366 B2 | 8/2010 | Maurer et al. | |
| 7,854,762 B2 | 12/2010 | Speziali et al. | |
| 7,942,928 B2 | 5/2011 | Webler et al. | |
| 8,080,808 B2 | 12/2011 | Norris | |
| 8,092,525 B2 | 1/2012 | Eliasen et al. | |
| 8,449,606 B2 | 5/2013 | Eliasen et al. | |
| 8,460,370 B2 | 6/2013 | Zakay | |
| 8,486,136 B2 | 7/2013 | Maurer et al. | |
| 8,579,967 B2 | 11/2013 | Webler et al. | |
| 8,758,432 B2 | 6/2014 | Solem | |
| 8,932,348 B2 | 1/2015 | Solem et al. | |
| 9,636,223 B2 * | 5/2017 | Khalil | A61F 2/2463 |
| 2003/0050694 A1 | 3/2003 | Yang et al. | |
| 2005/0038508 A1 | 2/2005 | Gabbay | |
| 2007/0093890 A1 | 4/2007 | Eliasen et al. | |
| 2007/0198082 A1 * | 8/2007 | Kapadia | A61B 17/00234 623/2.11 |
| 2007/0282429 A1 | 12/2007 | Hauser et al. | |
| 2008/0288061 A1 | 11/2008 | Maurer et al. | |
| 2009/0048668 A1 | 2/2009 | Wilson et al. | |
| 2009/0131880 A1 | 5/2009 | Speziali et al. | |
| 2009/0137968 A1 | 5/2009 | Rottenberg | |
| 2010/0198347 A1 | 8/2010 | Zakay et al. | |
| 2010/0298929 A1 | 11/2010 | Thornton et al. | |
| 2011/0077733 A1 | 3/2011 | Solem | |
| 2011/0224784 A1 * | 9/2011 | Quinn | A61B 17/00234 623/2.11 |
| 2011/0288577 A1 | 11/2011 | Newhauser et al. | |
| 2013/0190798 A1 * | 7/2013 | Kapadia | A61F 2/246 606/195 |
| 2013/0325110 A1 | 12/2013 | Khalil et al. | |
| 2013/0338763 A1 | 12/2013 | Rowe et al. | |

* cited by examiner

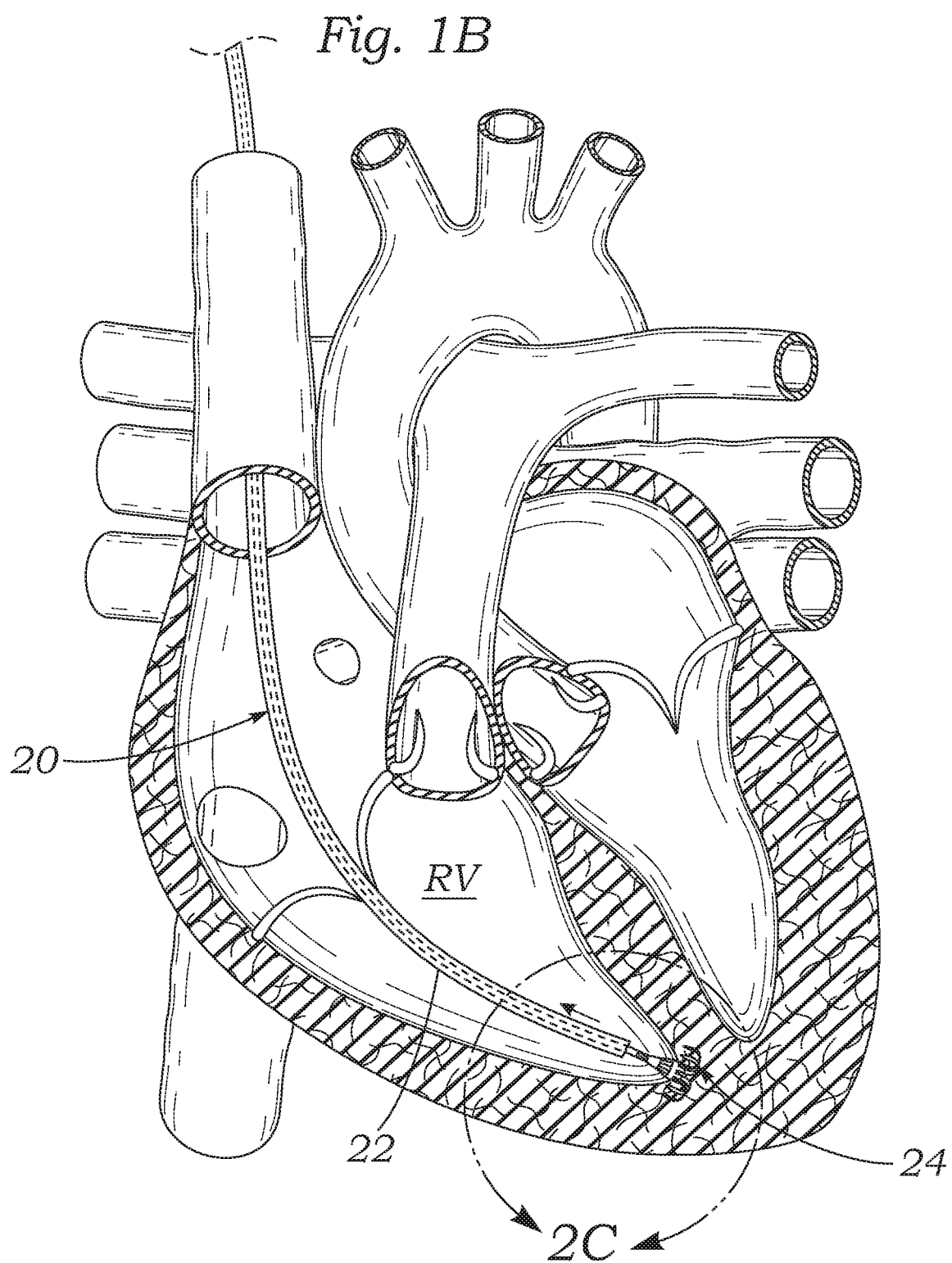

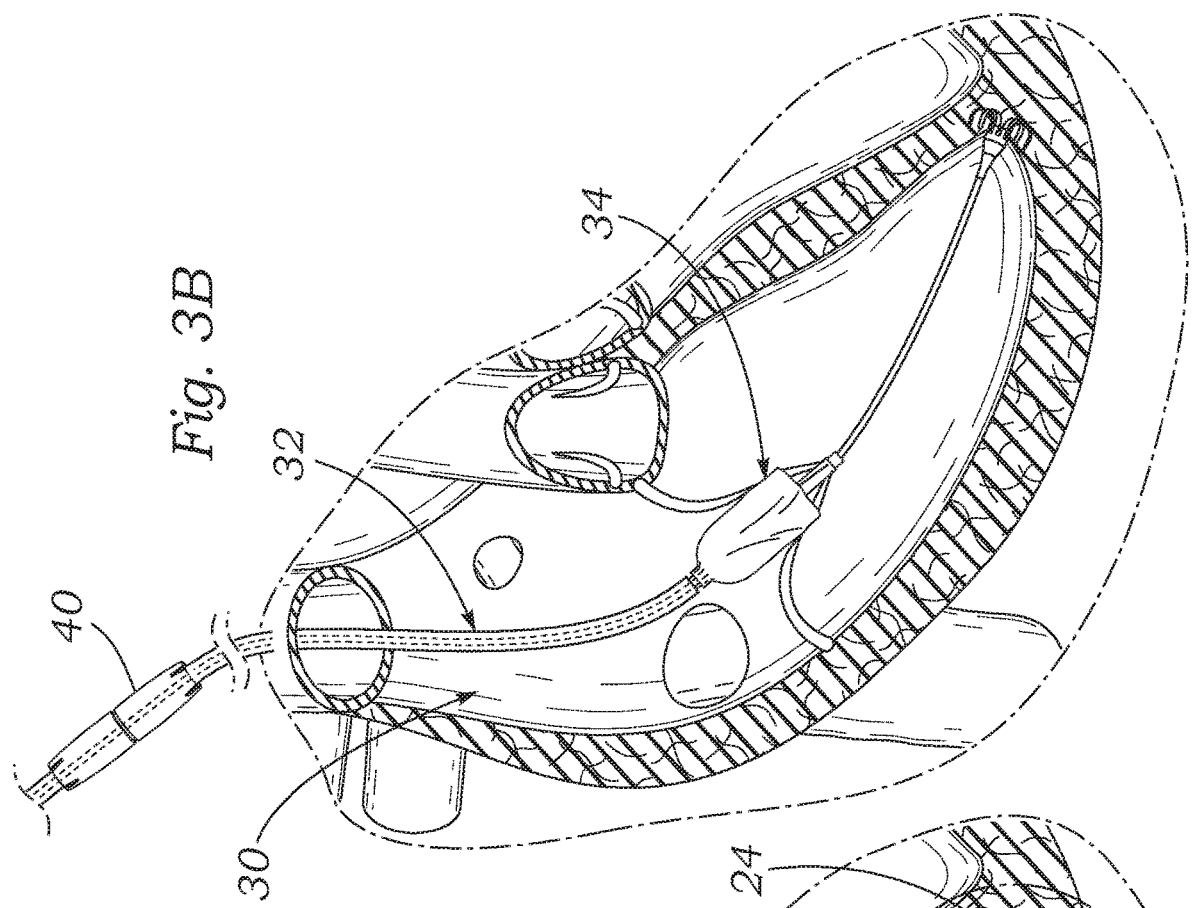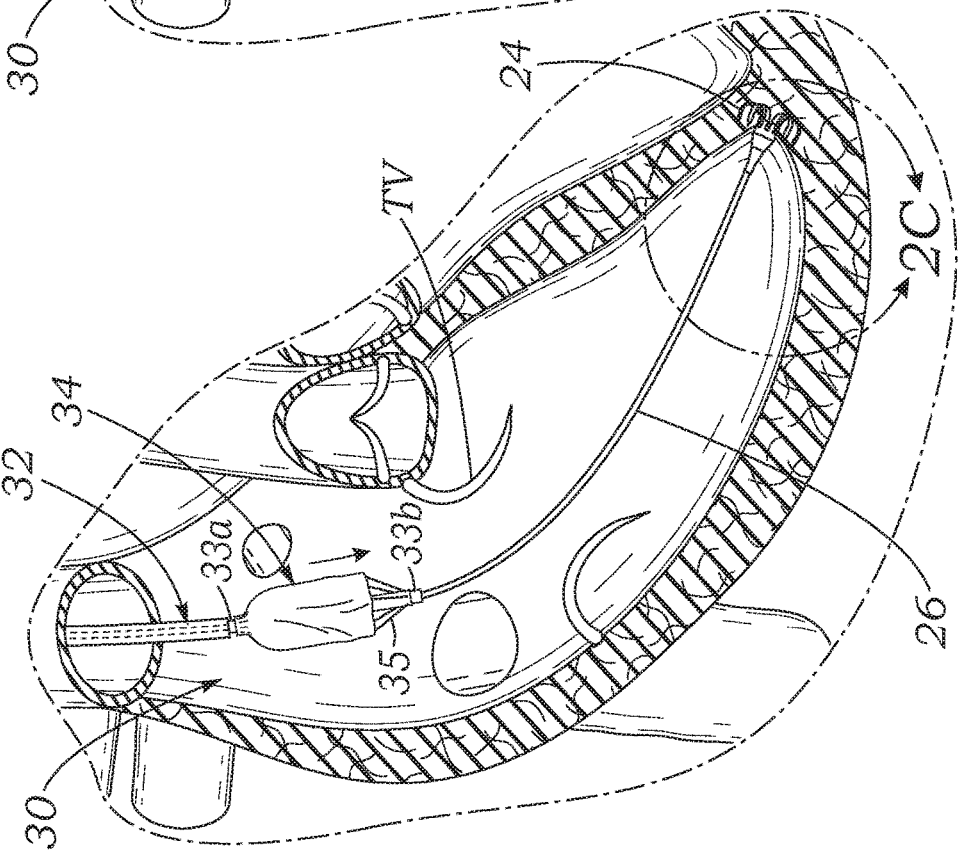

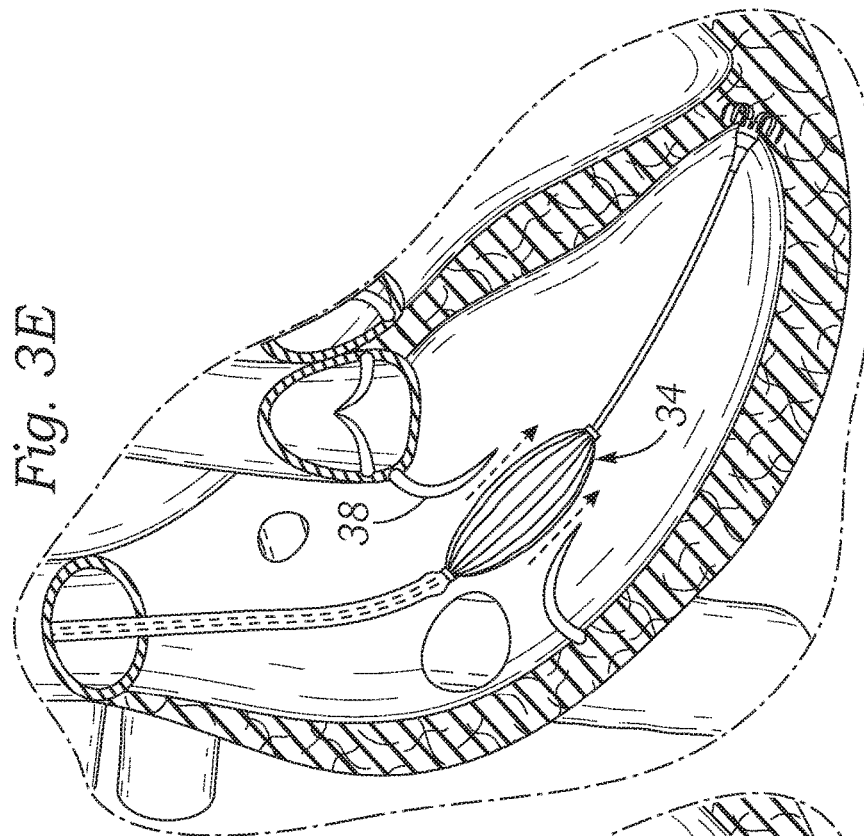
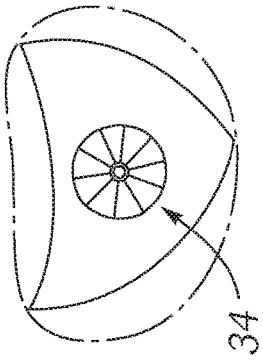
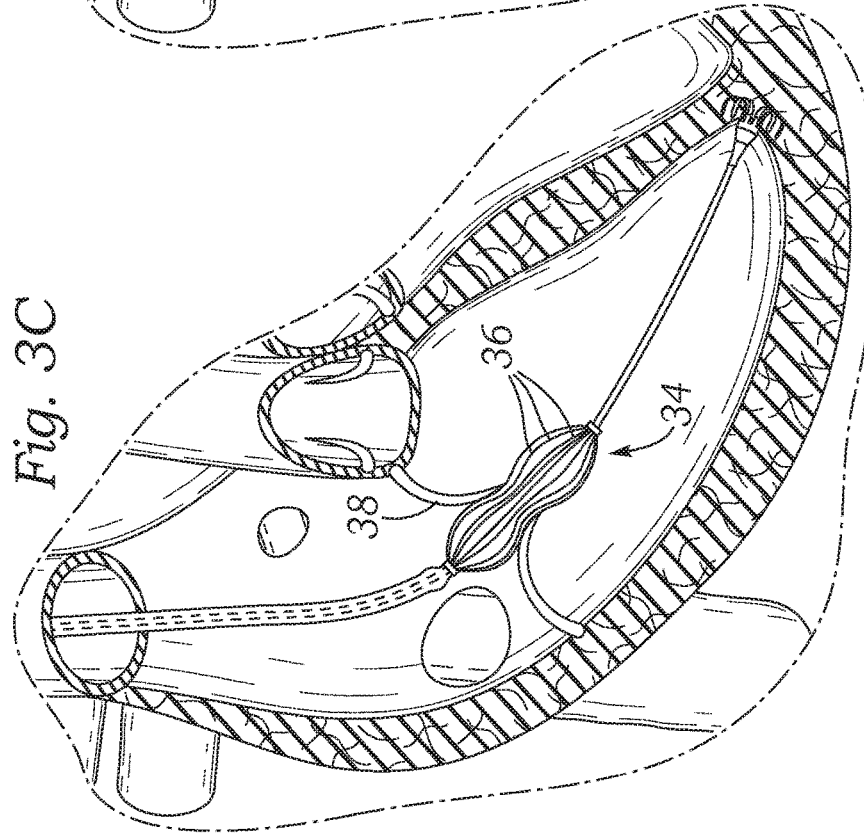
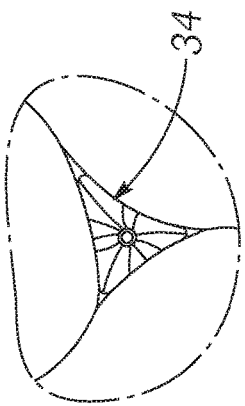

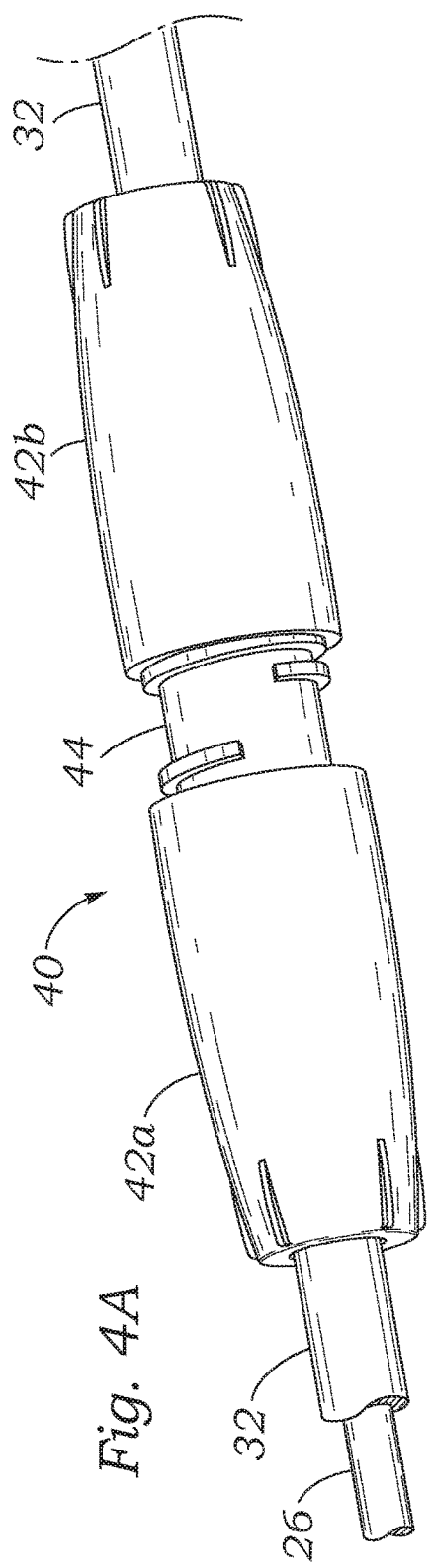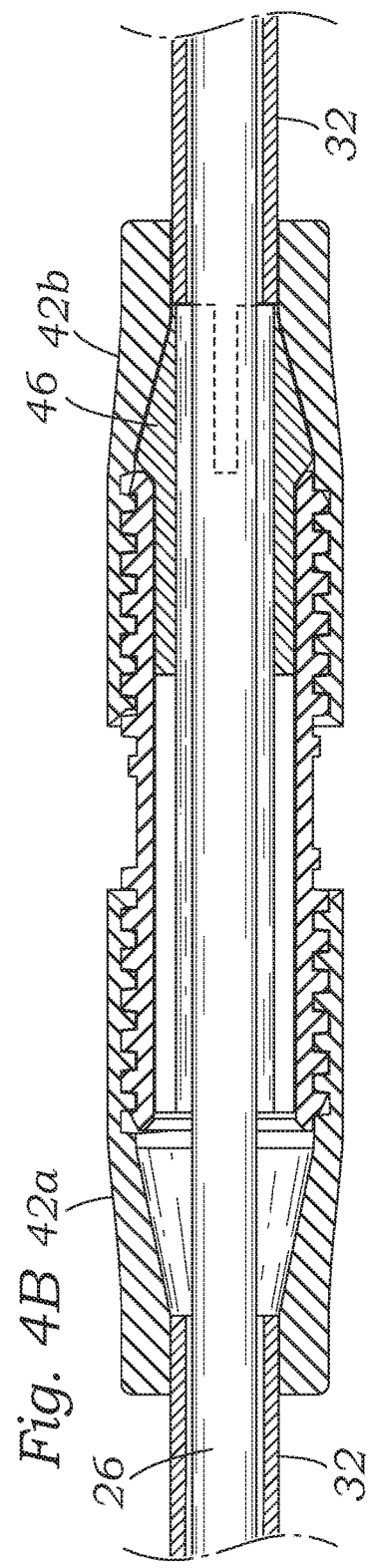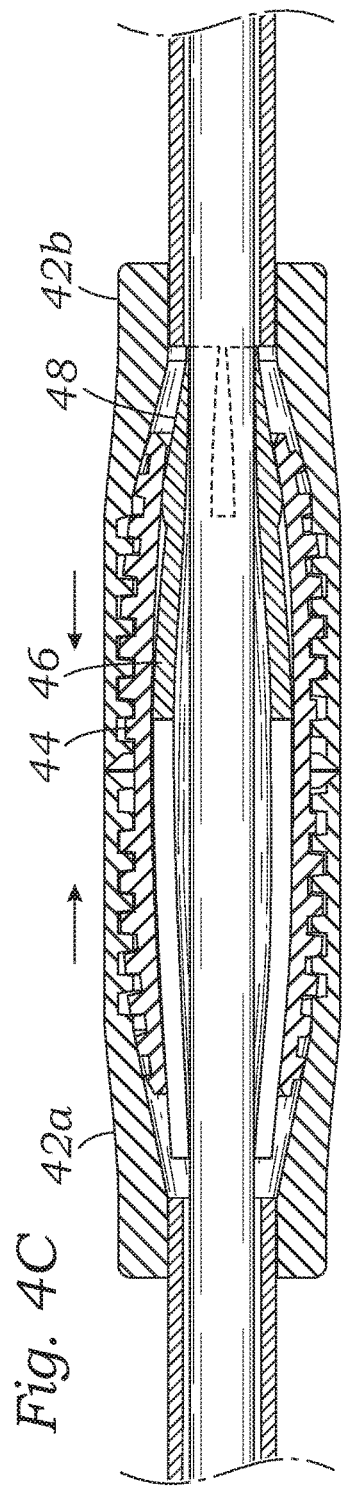

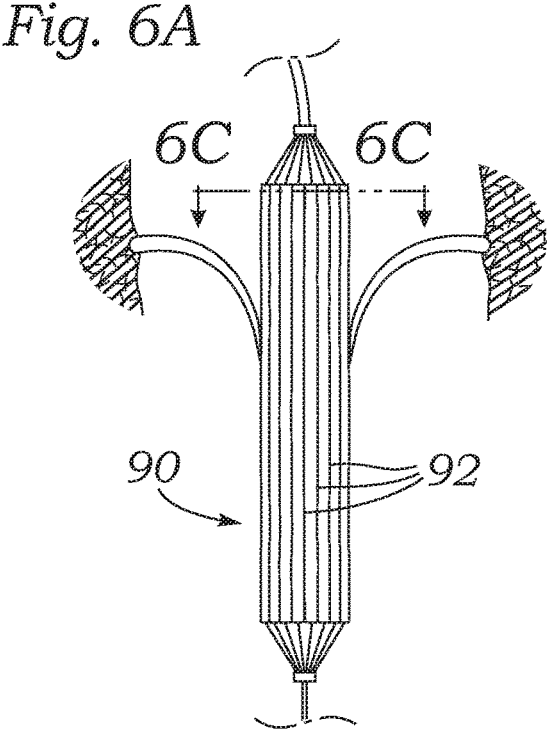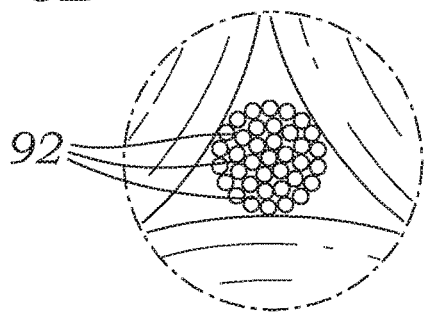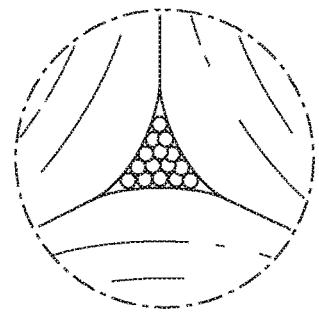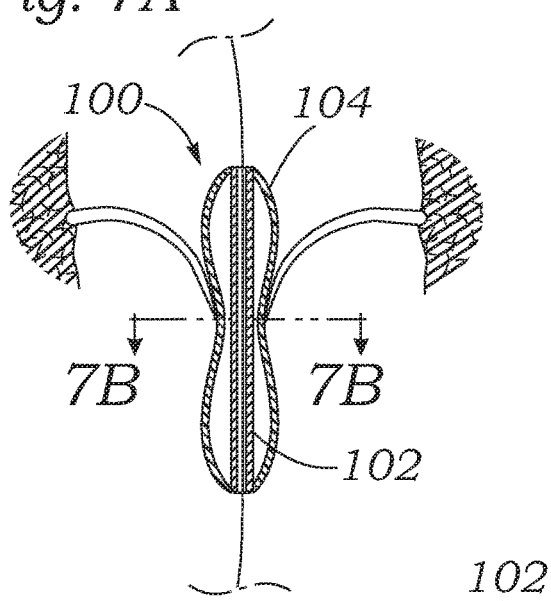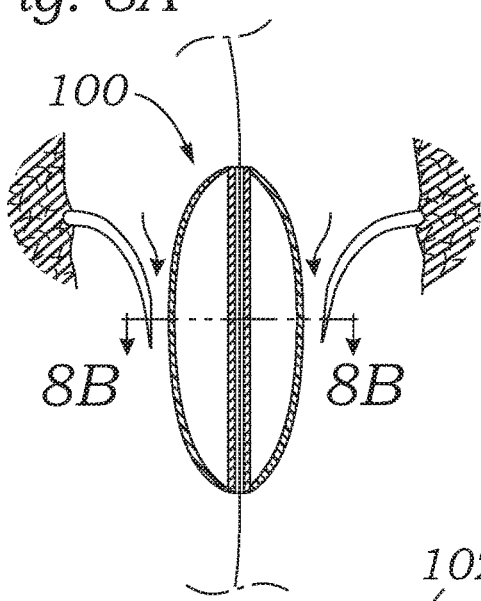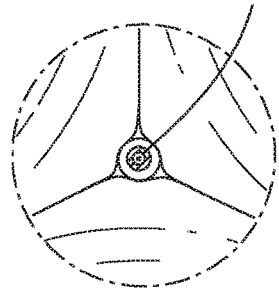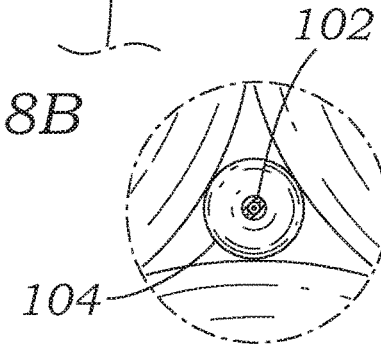

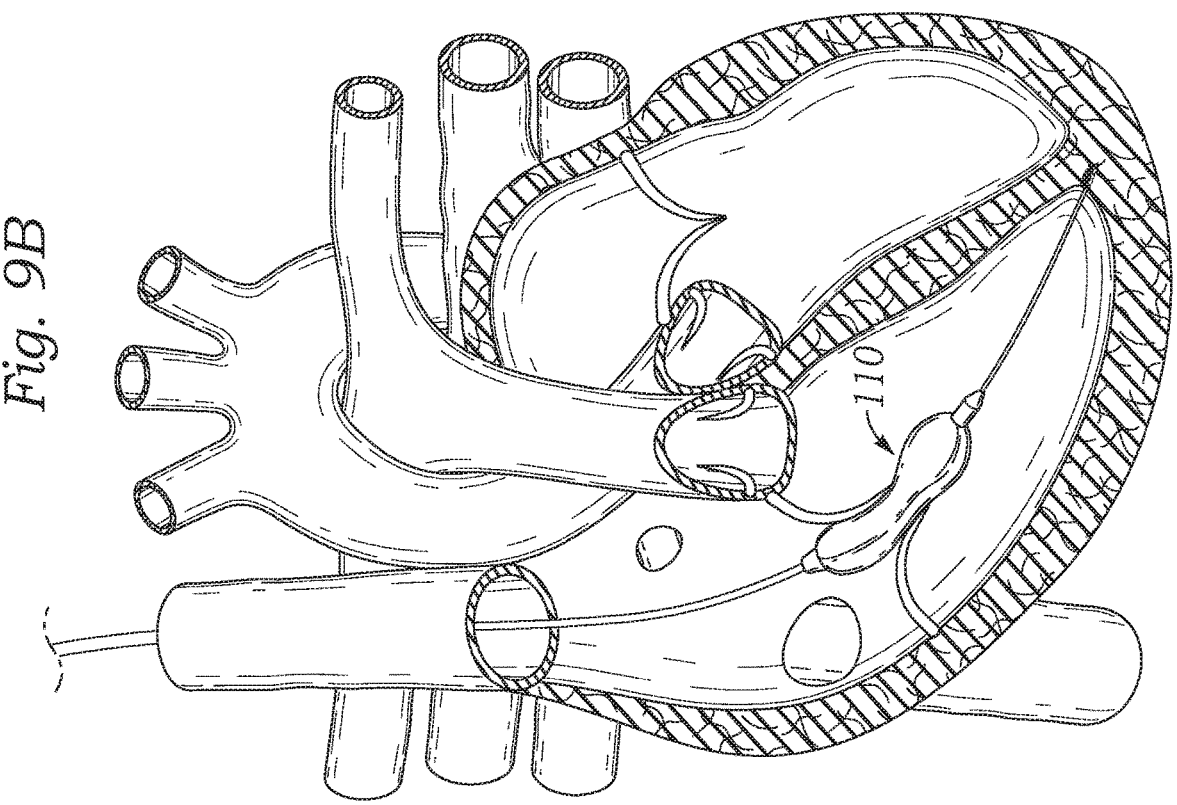
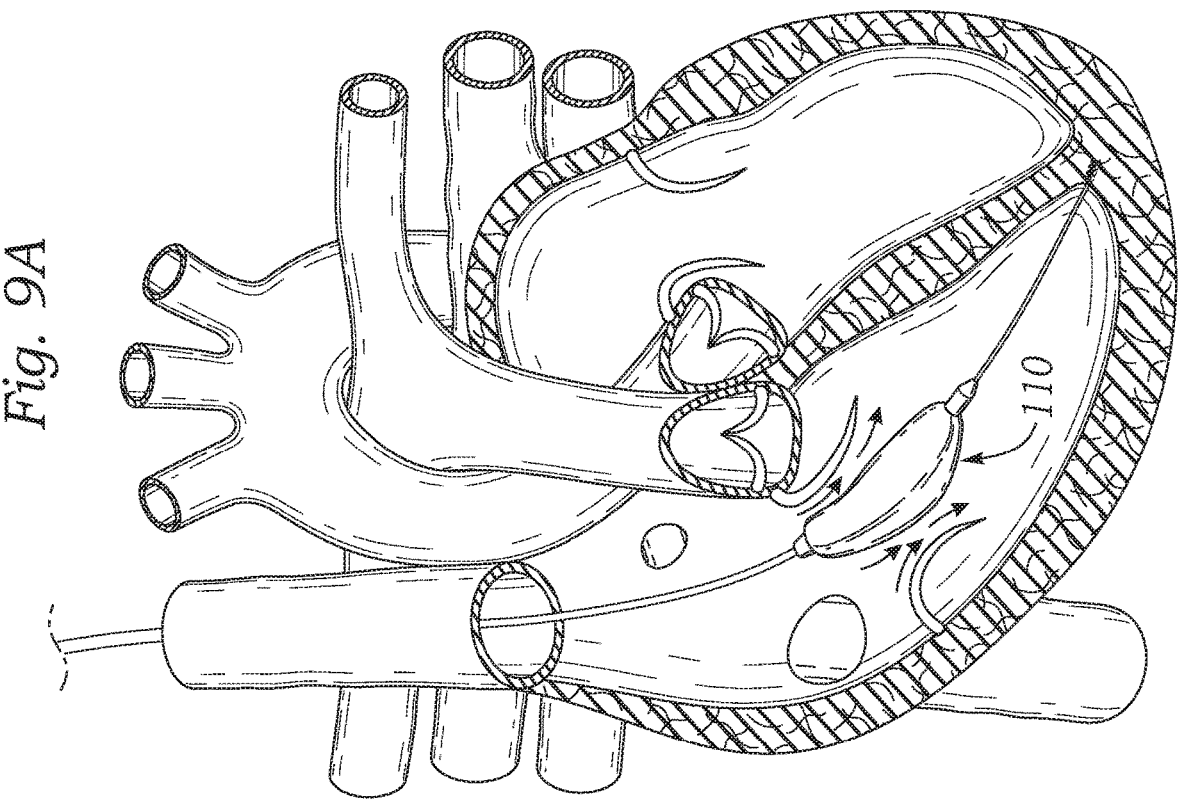

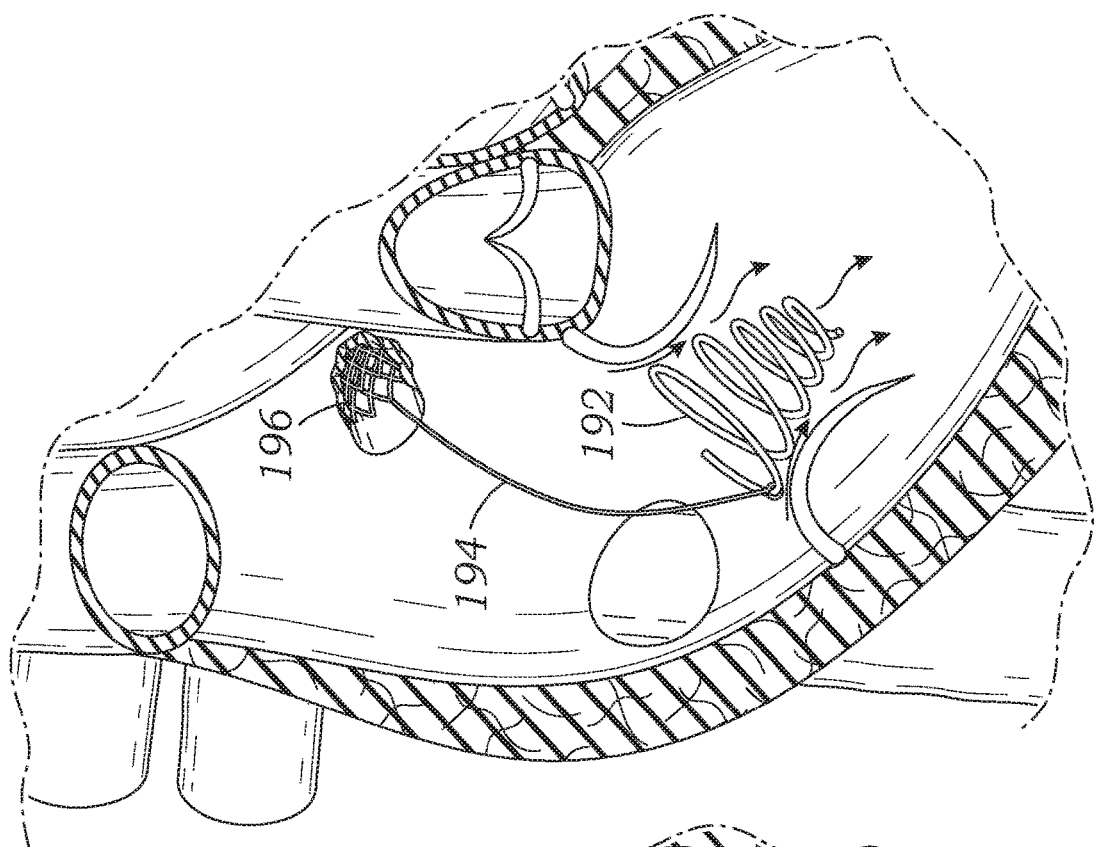
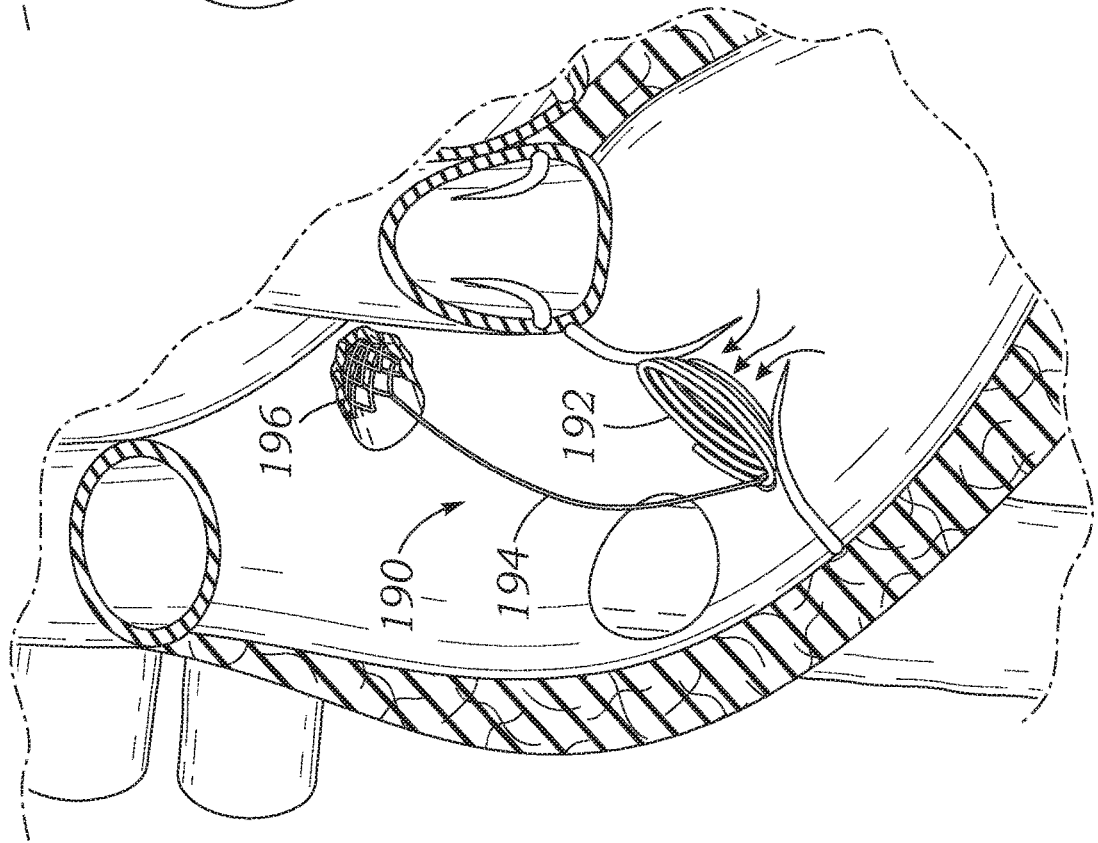

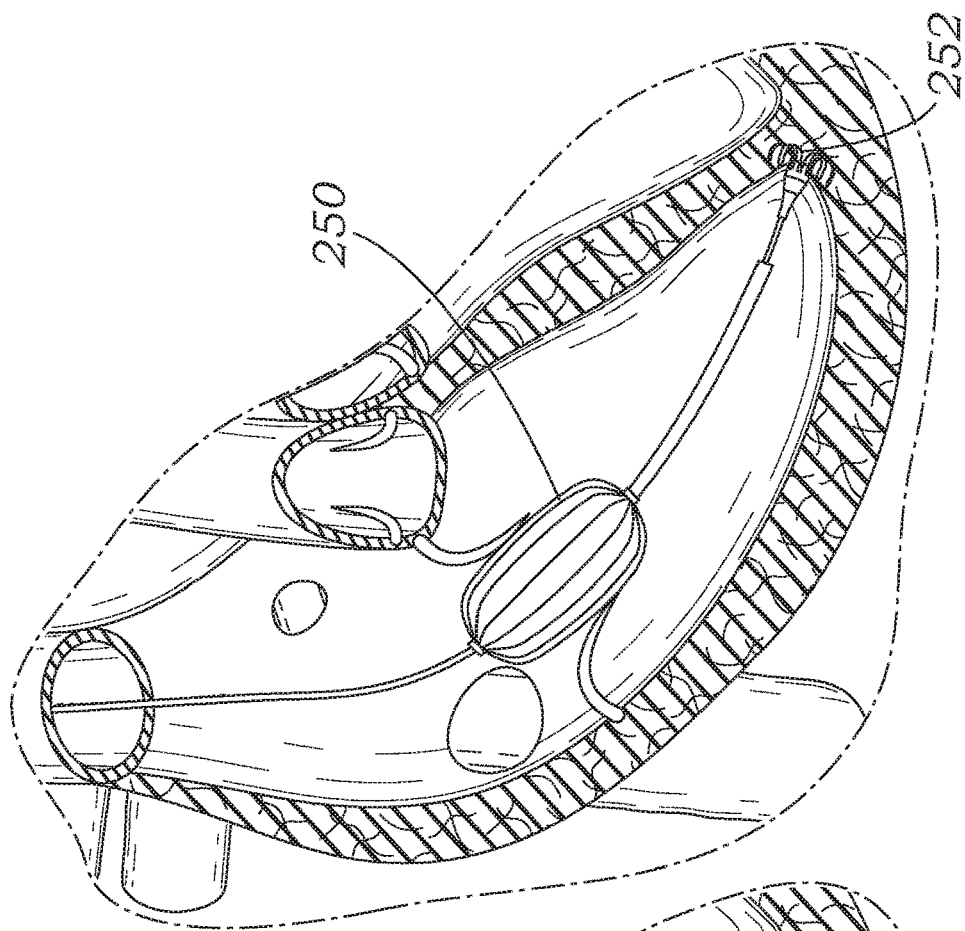
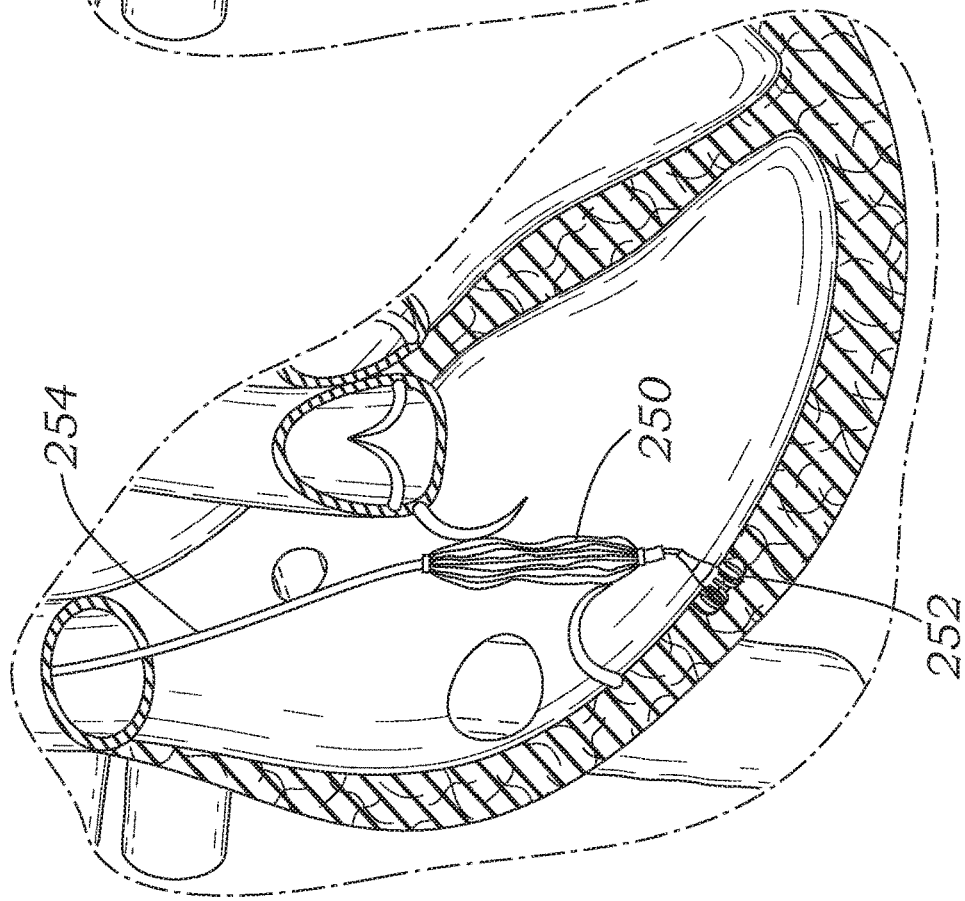

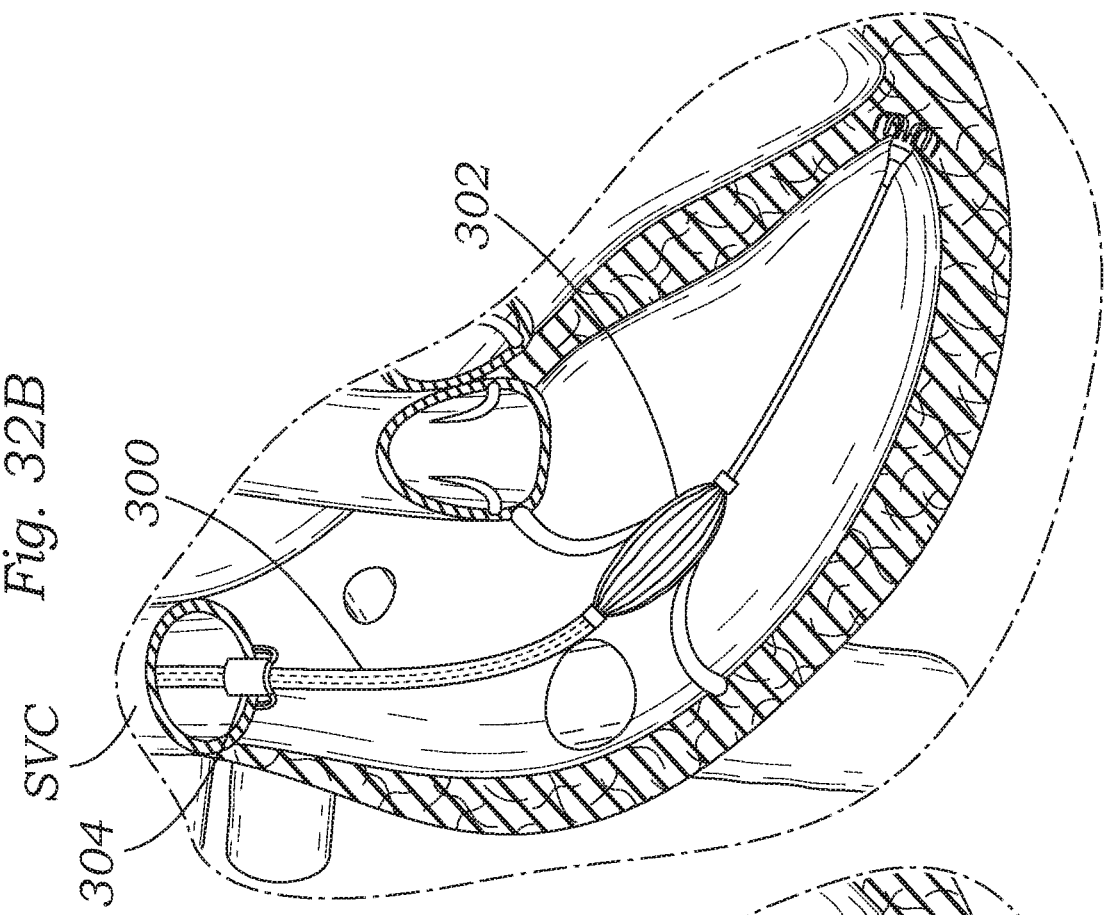
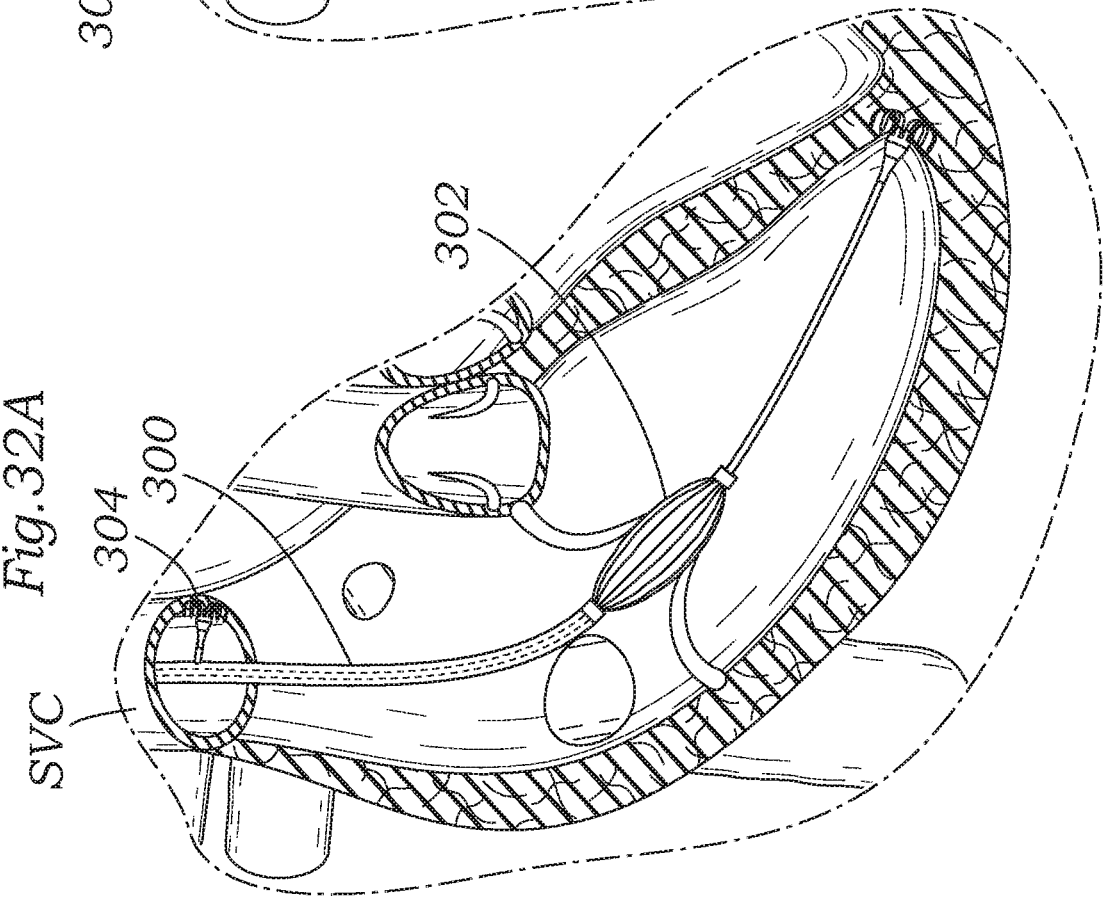

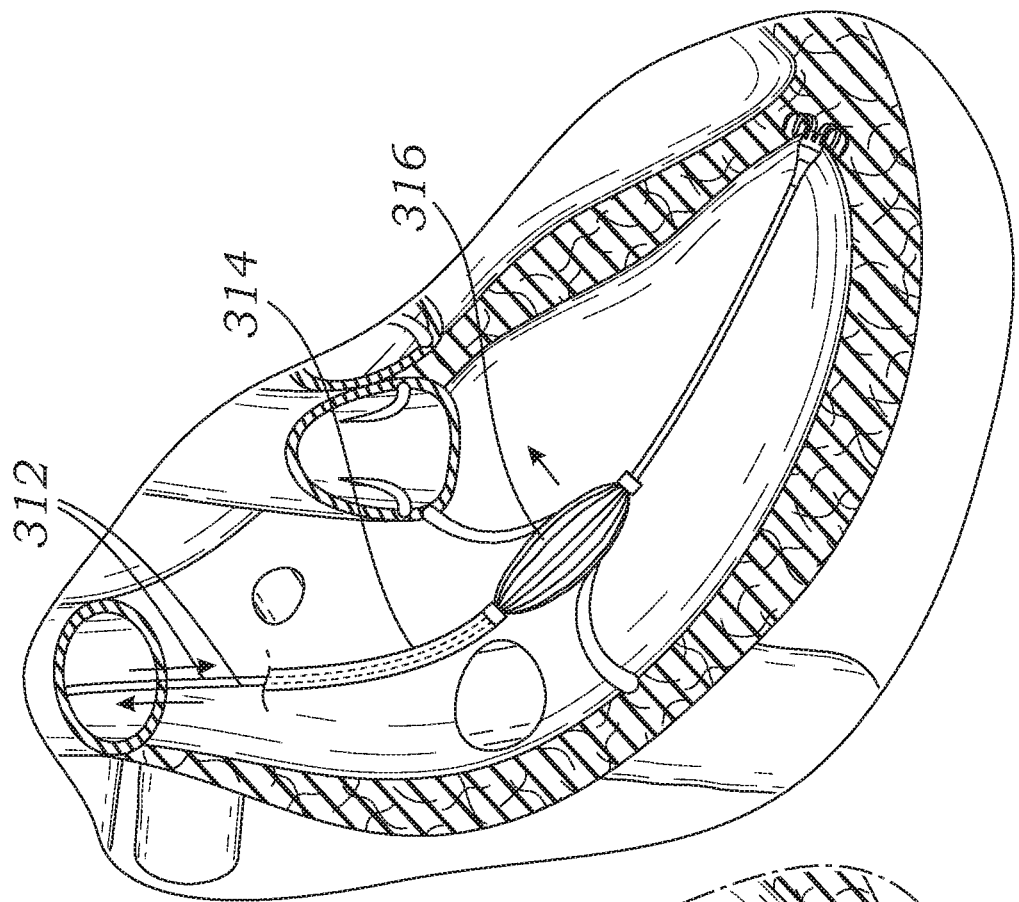
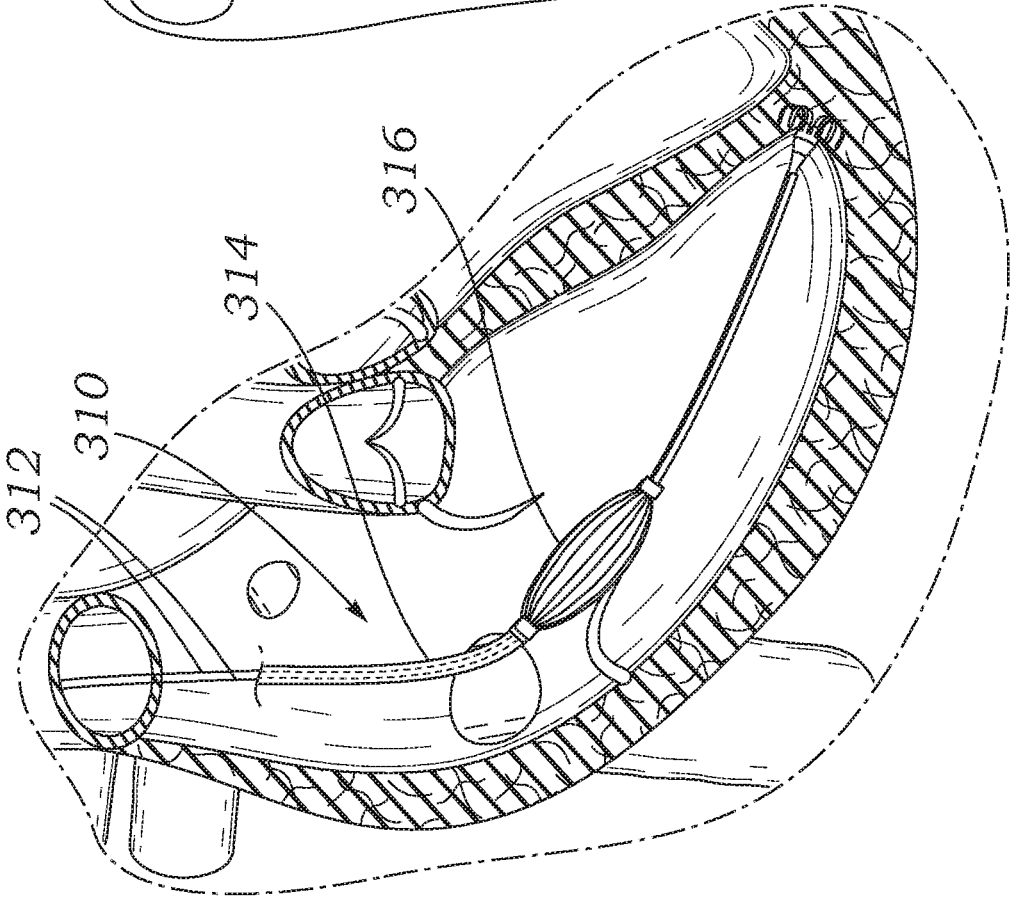

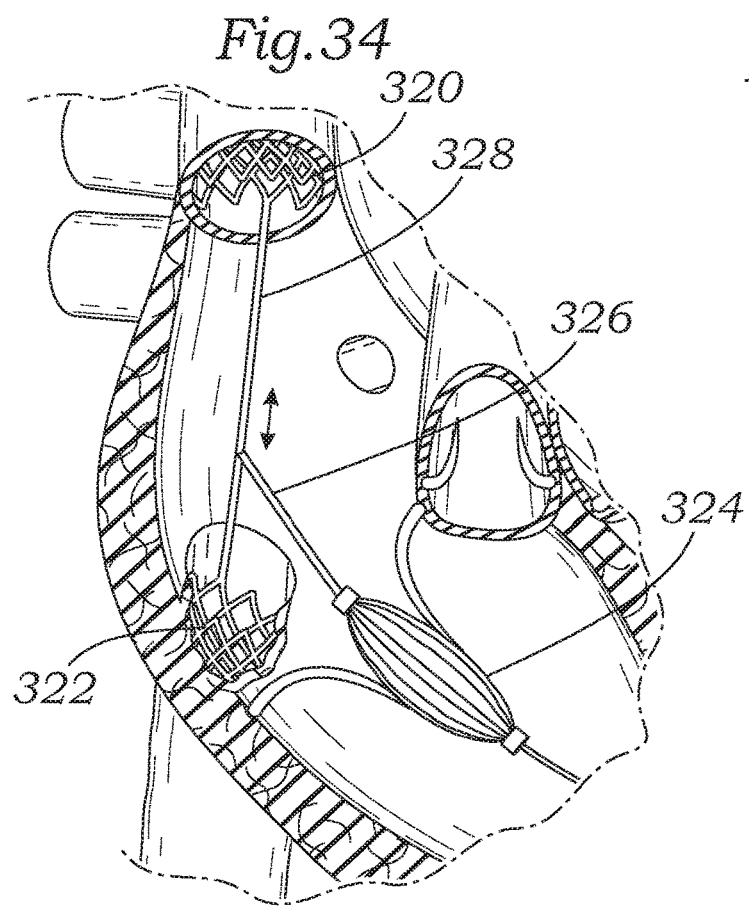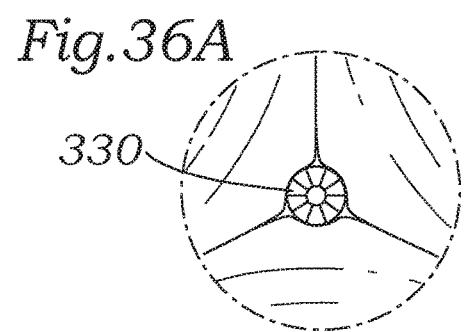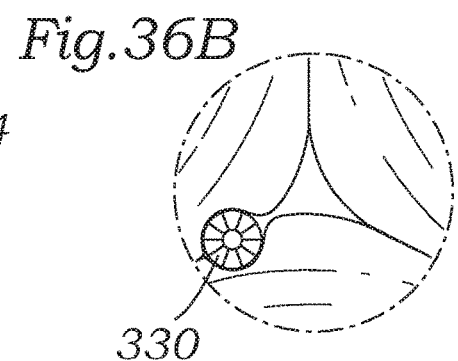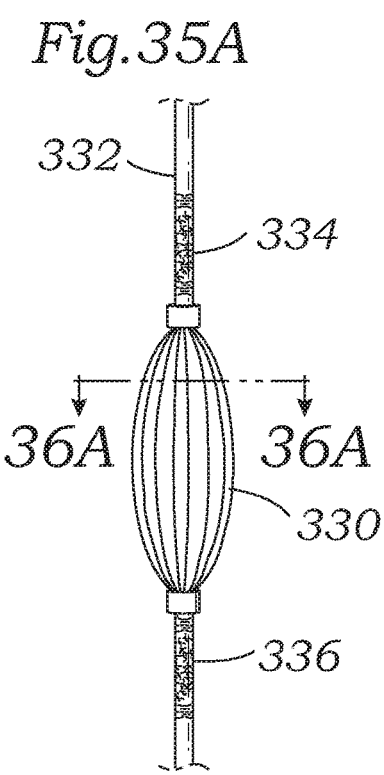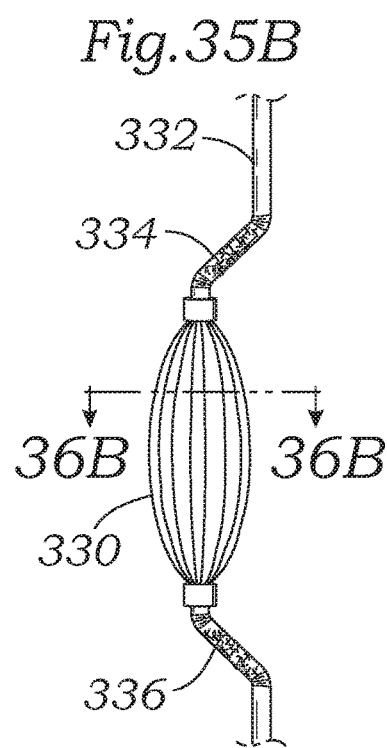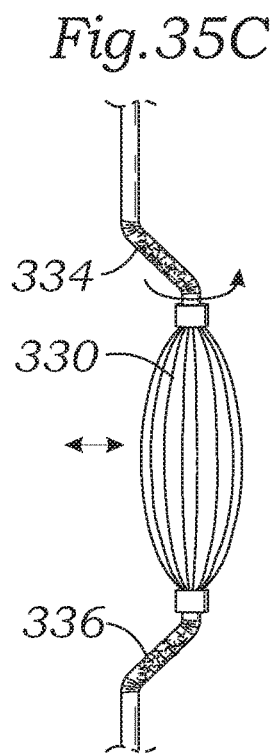

SYSTEMS FOR PLACING A COAPTING MEMBER BETWEEN VALVULAR LEAFLETS

RELATED APPLICATIONS

The present application is a continuation of U.S. application Ser. No. 13/895,611, filed May 16, 2013, which claims priority under 35 U.S.C. § 119 to U.S. Provisional Application Ser. No. 61/647,973, filed May 16, 2012, and to U.S. Provisional Application Ser. No. 61/734,728, filed Dec. 7, 2012, the disclosures of which are expressly incorporated herein by reference.

FIELD OF THE INVENTION

The present invention relates generally to devices and methods for improving the function of a defective heart valve. The devices and methods disclosed herein are particularly well adapted for implantation in a patient's heart for reducing regurgitation through a heart valve.

BACKGROUND OF THE INVENTION

The function of the heart may be seriously impaired if any of the heart valves are not functioning properly. The heart valves may lose their ability to close properly due to e.g. dilation of an annulus around the valve, ventricular dilation, or a leaflet being flaccid causing a prolapsing leaflet. The leaflets may also have shrunk due to disease, e.g. rheumatic disease, and thereby leave a gap in the valve between the leaflets. The inability of the heart valve to close properly can cause a leak backwards (i.e., from the outflow to the inflow side), commonly referred to as regurgitation, through the valve. Heart valve regurgitation may seriously impair the function of the heart since more blood will have to be pumped through the regurgitating valve to maintain adequate circulation. Heart valve regurgitation decreases the efficiency of the heart, reduces blood circulation, and adds stress to the heart. In early stages, heart valve regurgitation leaves a person fatigued or short of breath. If left unchecked, the problem can lead to congestive heart failure, arrhythmias or death.

Heart valve disease, such as valve regurgitation, is typically treated by replacing or repairing the diseased valve during open-heart surgery. However, open-heart surgery is highly invasive and is therefore not an option for many patients. For high-risk patients, a less-invasive method for repair of heart valves is considered generally advantageous.

Accordingly, there is an urgent need for an alternative device and method of use for treating heart valve disease in a minimally invasive procedure that does not require extracorporeal circulation. It is especially desirable that embodiments of such a device and method be capable of reducing or eliminating regurgitation through a tricuspid heart valve. It is also desirable that embodiments of such a device and method be well-suited for treating a mitral valve. It is also desirable that such a device be safe, reliable and easy to deliver. It is also desirable that embodiments of such a device and method be applicable for improving heart valve function for a wide variety of heart valve defects. It is also desirable that embodiments of such a device and method be capable of improving valve function without replacing the native valve. The present invention addresses this need.

SUMMARY OF THE INVENTION

The present invention relates generally to devices and methods for improving the function of a defective heart valve. The devices and methods disclosed herein are particularly well adapted for implantation in a patient's heart for reducing regurgitation through a heart valve. The devices and methods disclosed herein are particularly useful in reducing regurgitation through the two atrioventricular (AV) valves, which are between the atria and the ventricles—i.e., the mitral valve and the tricuspid valve.

In one embodiment, the device comprises: an anchor to deploy in the tissue of the right ventricle, a flexible anchor rail connected to the anchor, a coaptation element that rides over the anchor rail, a catheter attached to the proximal end of the coaptation element, a locking mechanism to fix the position of the coaptation element relative to the anchor rail, and a proximal anchoring feature to fix the proximal end of the coaptation catheter subcutaneously in the subclavian vein.

In another particular embodiment, the coaptation element consists of a hybrid structure: a series of a plurality (preferably three or more) flexible metallic struts to define a mechanical frame structure or a compressible biocompatible material, and a covering of pericardium or some other biocompatible material to provide a coaptation surface around which the native leaflets can form a seal. The flexible struts desirably attach to a catheter shaft on their proximal and/or distal ends, and collapse into a smaller diameter in order to be delivered through a low profile sheath. In particular, the struts attach on one end or both to a catheter shaft, and are complete or interrupted, they typically extend the length of the element, extend out or inwards, and may be discrete struts or a more connected mesh. The mechanical frame typically expands to the larger shape passively upon exiting a protective sheath via shape memory properties (e.g. Nitinol), but could also be expanded via longitudinal compression of the catheter, a shape memory balloon or some other external force. Additionally, the coaptation element can be an open or closed structure, any biocompatible material and framework that allows for compressibility for delivery and expands either actively or passively upon delivery, can be various shapes, and can be a passive or active element that is responsive to the cardiac cycle to change shapes to accommodate the regurgitant orifice.

One particular beating heart method includes delivering a coaptation member to a position within native tricuspid heart valve leaflets to reduce regurgitation therethrough. A ventricular anchor advances on the distal end of a flexible rail from above the native tricuspid annulus into the right ventricle. The ventricular anchor is anchored within the right ventricle, and a coaptation member on a distal end of a delivery catheter is advanced over the flexible rail until the coaptation member is positioned within the native tricuspid heart valve leaflets. The physician adjusts the position of the coaptation member within the tricuspid annulus under visualization to reduce regurgitation through the tricuspid valve. Subsequently, the position of the delivery catheter is locked relative to the flexible rail by clamping a locking collet carried by the catheter onto the flexible rail, and the locking collet is subcutaneously secured outside the subclavian vein. Desirably, the locking collet includes two internally threaded tubular grips each attached to separate sections of the delivery catheter that engaged a common externally threaded tubular shaft member through which the flexible rail passes. A tubular wedge member interposed between the tubular shaft member and the flexible rail cams inward upon screwing the tubular grips toward each other over the tubular shaft member.

Another beating heart method described herein for reducing regurgitation comprises advancing a ventricular anchor on the distal end of a flexible rail from above the native tricuspid annulus into the right ventricle, then advancing a catheter having a balloon thereon over the flexible rail until the balloon is positioned substantially within the tricuspid heart valve leaflets. The balloon on the catheter is inflated to center the flexible rail within the tricuspid annulus, and the flexible rail further advanced until the ventricular anchor is located approximately at the apex of the right ventricle, whereupon the ventricular anchor is anchored within the right ventricle. The catheter having the balloon may be the same as the catheter having the coaptation member, or an accessory catheter may be used. The physician then advances a coaptation member on a distal end of a delivery catheter over the flexible rail until the coaptation member is positioned within the native tricuspid heart valve leaflets. If an accessory catheter is used, the physician first removes the accessory catheter from the flexible rail. The position of the coaptation member within the tricuspid annulus is adjusted under visualization to reduce regurgitation through the tricuspid valve, and the position of the delivery catheter locked relative to the flexible rail.

A still further beating heart method of delivering a coaptation member to a native tricuspid heart valve leaflets includes again advancing a ventricular anchor on the distal end of a flexible rail from above the native tricuspid annulus into the right ventricle, and anchoring the ventricular anchor within the right ventricle. A coaptation member on a distal end of a delivery catheter advances over the flexible rail until the coaptation member is positioned within the native tricuspid heart valve leaflets. The coaptation member on the delivery catheter is then secured to a point above the tricuspid annulus and within a direct line to the tricuspid annulus. The physician adjusts the position of the coaptation member within the tricuspid annulus under visualization to reduce regurgitation through the tricuspid valve, and locks the position of the delivery catheter relative to the flexible rail.

The coaptation member may connect via a tether to a stent secured within a coronary sinus opening to the right atrium, or the coaptation member on the delivery catheter may be suspended within the annulus via flexible cables to a pair of anchors secured directly to the tricuspid annulus. Alternatively, the delivery catheter connects via an adjustable sleeve and a rod to an anchor secured within a coronary sinus opening to the right atrium, the adjustable sleeve and rod permitting adjustment of the relative positions of the anchor and the coaptation member. Another configuration involves connecting the delivery catheter directly to the superior vena cava via an anchor. Still further, the coaptation member may connect via a connecting wire or rod to two stent structures, one expanded in the superior vena cava and the other in the inferior vena cava.

In one embodiment, a spring is provided on the flexible rail between the coaptation member and the ventricular anchor so that the coaptation member can move axially with respect to the tricuspid annulus from compression and expansion of the spring. In another configuration, the delivery catheter includes a pair of relatively flexible regions directly proximal and distal to the coaptation member and a distal section of the delivery catheter locks down on the flexible rail. The step of adjusting the position of the coaptation member within the tricuspid annulus thus includes advancing and compressing the delivery catheter to cause the two flexible sections to buckle and displace the coaptation member laterally with respect to the catheter axis. The ventricular anchor may comprise a pair of concentric corkscrew anchors, one having a clockwise orientation and the other having a counterclockwise orientation. The coaptation member preferably comprises a frame form from a plurality of struts that supports a bell-shaped tissue cover formed by one or more panels of bioprosthetic tissue or flexible polymer sewn around the struts of the frame, the coaptation member being open toward the right ventricle and closed toward the right atrium.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIG. 1B is a cutaway view of the human heart in a systolic phase showing retraction of the anchoring catheter after installing a device anchor at the apex of the right ventricle;

FIGS. 3A and 3B are sectional views of the right atrium and ventricle that illustrate deployment of a regurgitation reduction device including a delivery catheter advanced along an anchor rail to position a coapting element within the tricuspid valve;

FIG. 3C is a sectional view of the right atrium and ventricle in systole showing a frame-type collapsible coapting element, while FIG. 3D is a view looking down on the tricuspid valve showing the leaflets closed around the frame;

FIGS. 3E and 3F are views similar to FIGS. 3C-3D with the tricuspid valve open in diastole permitting blood flow around the frame-type coapting element;

FIGS. 4A-4C are perspective and longitudinal sectional views of a locking collet shown proximally positioned on the catheter of FIGS. 3A and 3B that is used to fix the position of the delivery catheter and coapting element relative to the anchor rail;

FIGS. 6A-6C illustrate a coapting element having a series of aligned elongated members showing the tricuspid valve in both diastole and systole, respectively;

FIGS. 7A/7B show a coapting element having a more conventional balloon shape with the tricuspid valve in systole, while FIGS. 8A/8B show the same coapting element and the tricuspid valve in diastole;

FIGS. 9A-9B are sectional views of the heart illustrating a regurgitation reduction device positioned in the right atrium/right ventricle and having a three-sided frame as a coaptation element;

FIGS. 20A and 20B are systolic and diastolic views, respectively, of a tricuspid valve interacting with a coil-spring coapting element anchored by a stent within a coronary sinus;

FIG. 24 is a partial sectional view of an alternative anchoring device having concentric corkscrew anchors, while

FIGS. 27A and 27B show operation of a centering balloon that helps ensure proper positioning of an anchoring member at the apex of the right ventricle;

FIGS. 32A and 32B show two ways to anchor the delivery catheter to the superior vena cava for stabilizing the coapting element;

FIGS. 33A and 33B show a regurgitation reduction device having pull wires extending therethrough for altering the position of the coapting element within the tricuspid valve leaflets;

FIG. 34 shows a regurgitation reduction device anchored with stents in both the superior and inferior vena cava and having rods connecting the stents to the atrial side of the coapting element; and FIGS. 35A-35C and 36A-36B are schematic views of a coapting element mounted for lateral movement on a flexible delivery catheter that collapses and allows rotation for seating centrally in the valve plane even if the delivery catheter is not central.

DETAILED DESCRIPTION OF THE PREFERRED EMBODIMENTS

The following description refers to the accompanying drawings, which illustrate specific embodiments of the invention. Other embodiments having different structures and operation do not depart from the scope of the present invention.

Exemplary embodiments of the present disclosure are directed to devices and methods for improving the function of a defective heart valve. It should be noted that various embodiments of coapting elements and systems for delivery and implant are disclosed herein, and any combination of these options may be made unless specifically excluded. For example, any of the coapting elements disclosed may be combined with any of the flexible rail anchors, even if not explicitly described. Likewise, the different constructions of coapting elements may be mixed and matched, such as combining any tissue cover with any inner flexible support, even if not explicitly disclosed. In short, individual components of the disclosed systems may be combined unless mutually exclusive or otherwise physically impossible.

Figure 1A:
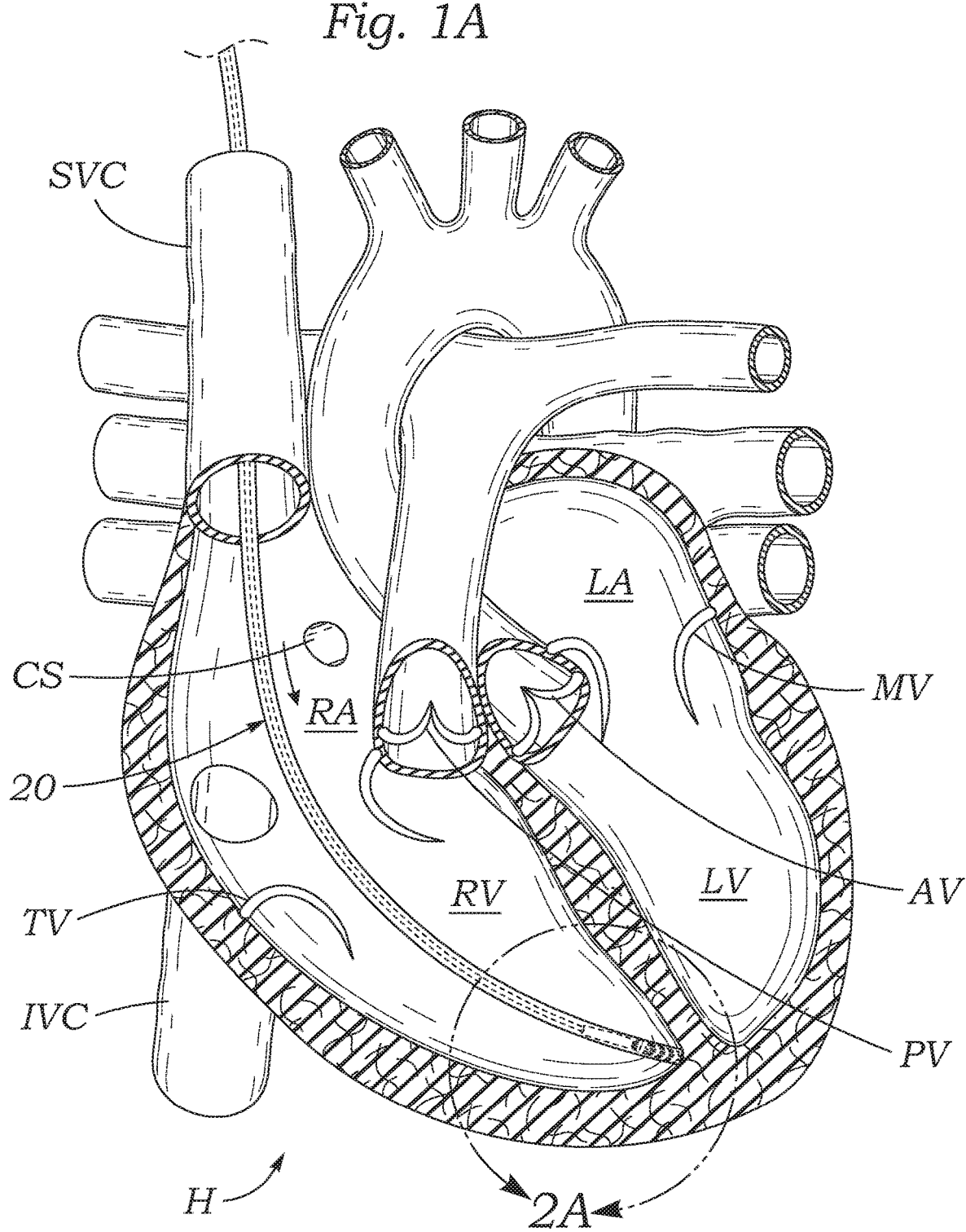
FIG. 1A is a cutaway view of the human heart in a diastolic phase showing introduction of an anchoring catheter into the right ventricle as a first step in deploying a device of the present application for reducing tricuspid valve regurgitation.

FIGS. 1A and 1B are cutaway views of the human heart in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta (not identified) and the pulmonary valve PV separates the right ventricle from the pulmonary artery (also not identified). Each of these valves has flexible leaflets extending inward across the respective orifices that come together or "coapt" in the flowstream to form the one-way fluid occluding surfaces. The regurgitation reduction devices of the present application are primarily intended for use to treat the atrioventricular valves, and in particular the tricuspid valve. Therefore, anatomical structures of the right atrium RA and right ventricle RV will be explained in greater detail, though it should be understood that the devices described herein may equally be used to treat the mitral valve MV.

The right atrium RA receives deoxygenated blood from the venous system through the superior vena cava SVC and the inferior vena cava IVC, the former entering the right atrium above, and the latter from below. The coronary sinus CS is a collection of veins joined together to form a large vessel that collects deoxygenated blood from the heart muscle (myocardium), and delivers it to the right atrium RA. During the diastolic phase, or diastole, seen in FIG. 1A, the venous blood that collects in the right atrium RA is pulled through the tricuspid valve TV by expansion of the right ventricle RV. In the systolic phase, or systole, seen in FIG. 1B, the right ventricle RV collapses to force the venous blood through the pulmonary valve PV and pulmonary artery into the lungs. During systole, the leaflets of the tricuspid valve TV close to prevent the venous blood from regurgitating back into the right atrium RA. It is during systole that regurgitation through the tricuspid valve TV becomes an issue, and the devices of the present application are beneficial.

Regurgitation Reduction System:

FIGS. 1A and 1B show introduction of an anchoring catheter 20 into the right ventricle as a first step in deploying a device of the present application for reducing tricuspid valve regurgitation. The anchoring catheter 20 enters the right atrium RA from the superior vena cava SVC after having been introduced to the subclavian vein (see FIG. 5) using well-known methods, such as the Seldinger technique. More particularly, the anchoring catheter 20 preferably tracks over a pre-installed guide wire (not shown) that has been inserted into the subclavian vein and steered through the vasculature until it resides at the apex of the right ventricle. The physician advances the anchoring catheter 20 along the guide wire until its distal tip is touching the ventricular apex, as seen in FIG. 1A.

FIG. 1B shows retraction of a sheath 22 of the anchoring catheter 20 after installing a device anchor 24 at the apex of the right ventricle RV. The sheath 22 has desirably been removed completely from the patient's body in favor of the second catheter, described below.

Figure 2A:
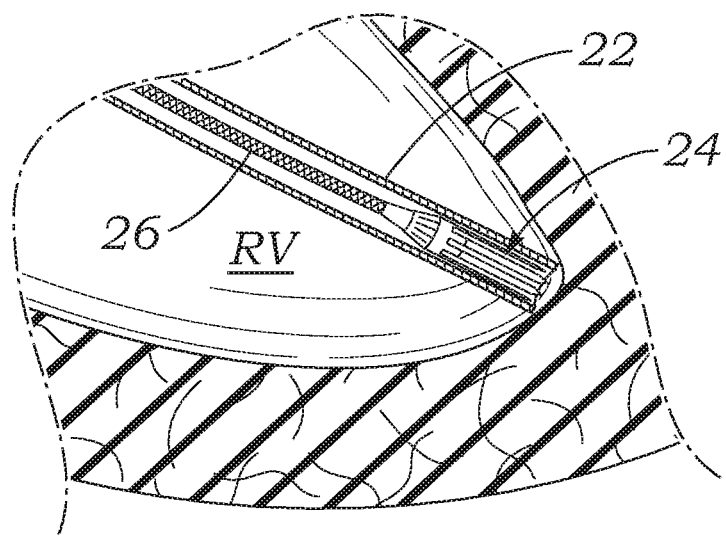
FIGS. 2A-2C are detailed views of installation of an exemplary device anchor by the anchoring catheter.
Figure 2B:
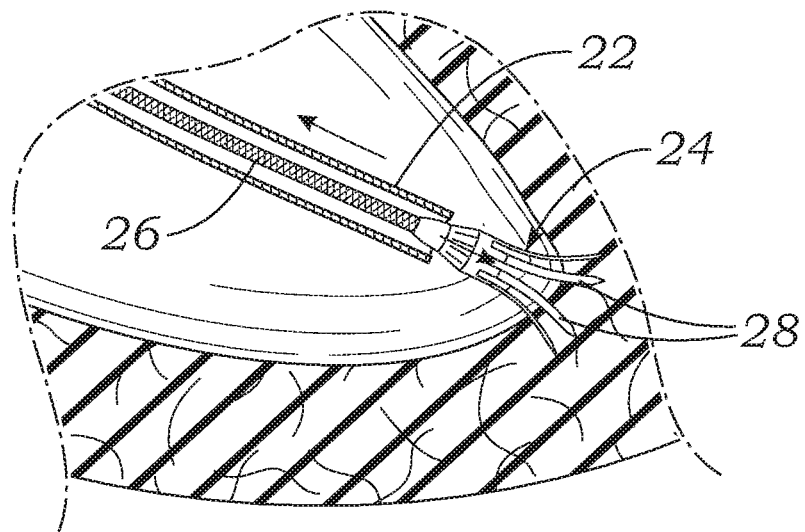
Figure 2C:
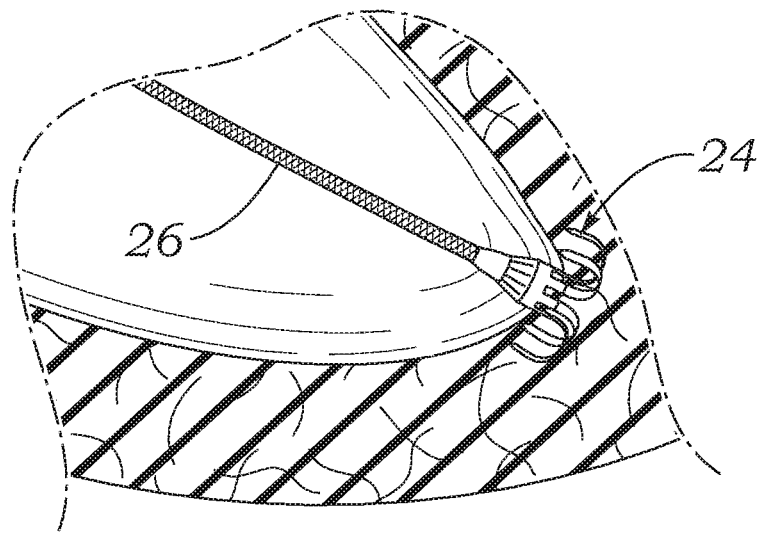

First, a detail explanation of the structure and usage of an exemplary device anchor 24 will be provided with reference to FIGS. 2A-2C. FIG. 2A is an enlargement of the distal end of the anchoring catheter sheath 22 in the position of FIG. 1A. The device anchor 24 is seen within the sheath 22 positioned just within the distal end thereof. The device anchor 24 attaches to an elongated anchor rail 26, which in some versions is constructed to have good capacity for torque. For instance, the anchor rail 26 may be constructed as a braided wire rod, or cable.

In FIG. 2B, the catheter sheath 22 is shown being retracted proximally, while the device anchor 24 and anchor rail 26 are expelled distally therefrom. The exemplary device anchor 24 includes a plurality of circumferentially distributed and distally-directed sharp tines or barbs 28 that pierce the tissue of the ventricular apex. The barbs 28 are held in a stressed configuration within the sheath 22, and are provided with an outward elastic bias so that they curl outward upon release from the sheath. Desirably the barbs 28 are made of a super-elastic metal such as Nitinol. The outward curling of the barbs 28 can be seen in both FIGS. 2B and 2C, the latter showing the final relaxed configuration of the barbs. The operation to embed the device anchor 24 may be controlled under visualization, such as by providing radiopaque markers in and around the device anchor 24 and distal end of the catheter sheath 22. Certain other devices described herein may be used to help position the device anchor 24 at the ventricular apex, as will be described. Although the particular device anchor 24 shown in FIGS. 2A-2C is considered highly effective, other anchors are contemplated, such as shown and described below, and the application should not be considered limited to one type or another.

To facilitate central positioning of the anchor rail 26 during deployment the device is implanted with the assistance of a fluoroscope. For example, after properly positioning the patient so as to maximize the view of the target annulus, for example the tricuspid annulus, a pigtail catheter is placed in the right ventricle and contrast injected. This allows the user to see a clear outline of the annulus and the right ventricle. At this point, a frame of interest is selected (e.g., end systole) in which the annulus is clearly visible and the annulus to ventricular apex distance is minimized. On the monitor, the outline of the right ventricle, the annulus, and the pulmonary artery are traced. The center of the annulus is then identified and a reference line placed 90° thereto is drawn extending to the right ventricular wall. This provides a clear linear target for anchoring. In a preferred embodiment, the anchor 24 is preferably located in the base of the ventricle between the septum and the free wall.

Aligning the anchor rail 26 in this manner helps center the eventual positioning of a coapting element of the system within the tricuspid leaflets. If the coapting element is offset to the anterior or posterior side, it may get stuck in the tricuspid valve commissures resulting in leakage in the center of the valve. An alternative method is to place a device such as a Swan Ganz catheter through the right ventricle and into the pulmonary artery to verify that the viewing plane is parallel to the anterior/posterior viewing plane. Addition of a septal/lateral view on the fluoroscope may be important to center the anchor in patients that have a dilated annulus and right ventricle.

Figures 5, 5A:
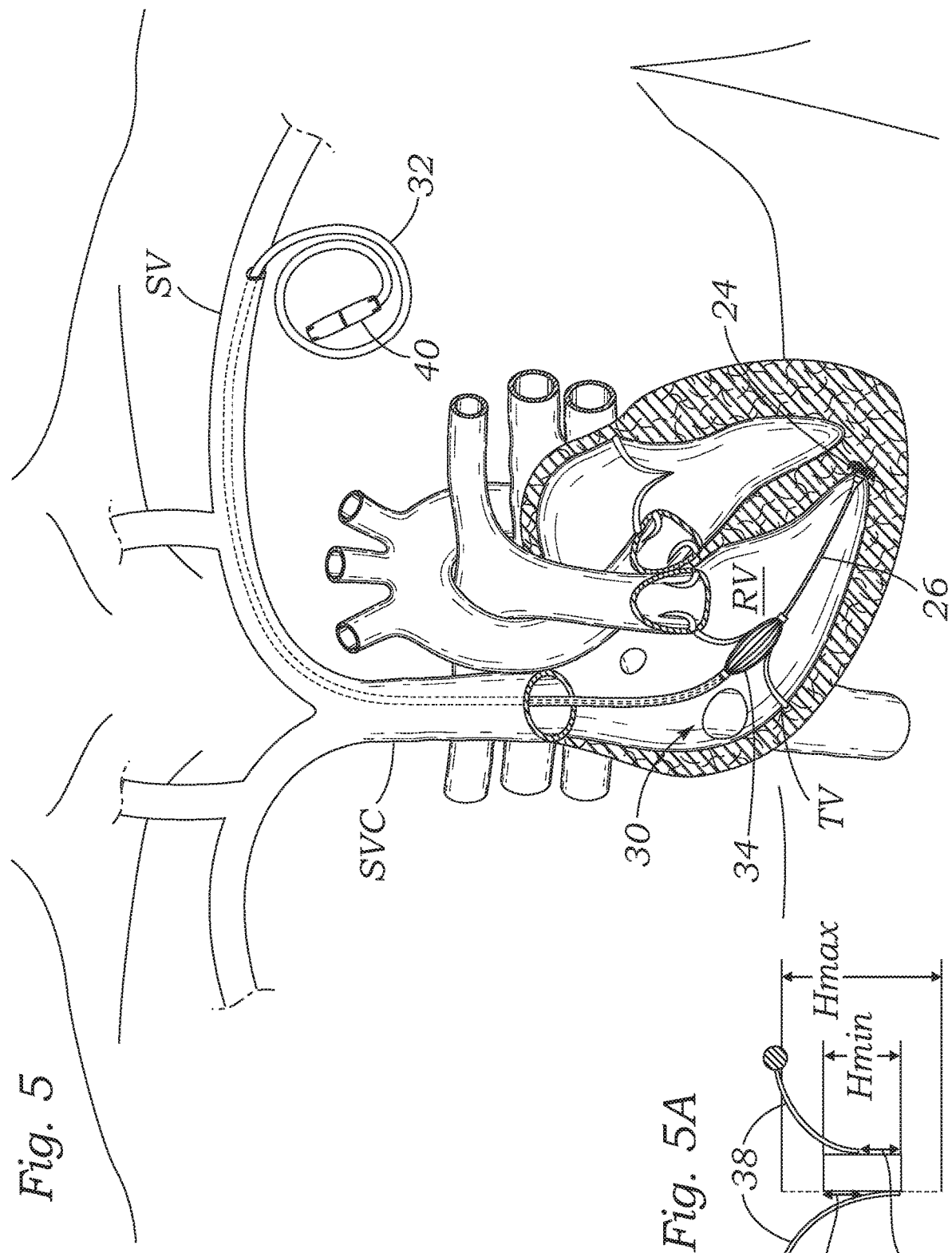
FIG. 5 is a broader view of the final configuration of the regurgitation reduction device of the present application with a coapting element positioned within the tricuspid valve and a proximal length of the delivery catheter including the locking collet shown exiting the subclavian vein to remain implanted subcutaneously.
FIG. 5A is a schematic diagram of a representative coapting element and a pair of native tissue leaflets indicating certain key dimensions used in constructing the coapting element.

FIGS. 3A and 3B illustrate deployment of a regurgitation reduction device 30 including a delivery catheter 32 advanced along the anchor rail 26 to position a coapting element 34 within the tricuspid valve TV. The coapting element 34 fastens to a distal end of the delivery catheter 32, both of which slide along the anchor rail 26, which has been previously positioned as described above. Ultimately, as seen in FIG. 3B, the coapting element 34 resides within the tricuspid valve TV, the leaflets of which are shown closed in systole and in contact with the coapting element. Likewise, the delivery catheter 32 remains in the body as seen in FIGS. 3B and 5, and the prefix "delivery" should not be considered to limit its function. A variety of coapting elements are described herein, the common feature of which is the goal of providing a plug of sorts within the heart valve leaflets to mitigate or otherwise eliminate regurgitation. In the illustrated embodiment, the coapting element 34 includes an inner strut structure partly surrounded by bioprosthetic tissue, as will be described in more detail below.

In one embodiment, a short tubular collar 33a fastens to the distal end of the delivery catheter 32 and provides structure to surround the proximal ends of a plurality of struts 35 that form a strut frame. A second tubular collar 33b holds together the distal ends of the struts 35 and attaches to a small ferrule (not shown) having a through bore that slides over the anchor rail 26. Each of the struts 35 has proximal and distal ends that are formed as a part of (or constrained within) these collars 33a, 33b and a mid-portion that arcs radially outward to extend substantially parallel to the axis of the coapting element 34. The frame shape is thus a generally elongated oval. In the illustrated embodiment, there are six struts 35 in the frame, although more or less could be provided. The struts 35 are desirably formed of a super-elastic material such as Nitinol so as to have a minimum amount of rigidity to form the generally cylindrical outline of the frame but maximum flexibility so that the frame deforms from the inward forces imparted by the heart valve leaflets.

The coapting element 34 may include a cover formed by one or more panels of bioprosthetic tissue or flexible polymer sewn around the struts 35 of the frame. One particularly effective polymer is a polycarbonate urethane (Carbothane from Lubrizol, Bionate from DSM, ChronoFlex from Advansource) which has extremely good durability over long periods of time, as opposed to materials such as Nylon used for typical catheter balloons. Alternatively, a polycarbonate silicone may also be used. A single axial seam may be used, though the cover is typically formed of two or three panels sewn together with a matching number of seams. The tissue cover may be formed of a variety of xenograft sheet tissue, though bovine pericardial tissue is particularly preferred for its long history of use in cardiac implants, physical properties and relative availability. Other options are porcine or equine pericardium, for example.

In the embodiment of FIGS. 3A-3B, the tissue cover has a proximal end that is closed to fluid flow, and a distal end that is open; thus, the cover resembles a bell shape. Desirably, the axial length of the cover extends from the proximal collar 33a approximately three-quarters of the way down to the distal collar 33b, to the end of the flat section of the device. As mentioned above, the open bell shape desirably facilitates functioning of the coapting element. Namely, during diastole, blood flows around the coaptation element 34, while during systole, as the native leaflets close and contact the coaptation element, the pressure and blood flow work to fill the interior of the coaptation element by pushing blood in, the interior of the coaptation element is at the same pressure as the RV and a seal is created. These phases of the cardiac cycle are common to both the tricuspid and mitral valves. Generally the coaptation elements that are closed on the atrial side and open to the ventricular side move essentially like a parachute—filling in systole, and blood flowing around without collapse in diastole.

FIG. 3C is a sectional view of the right atrium and ventricle in systole showing a balloon-type coapting element 34, while FIG. 3D shows the tricuspid valve leaflets 38 closed around the balloon. FIGS. 3E and 3F show the tricuspid valve open in diastole permitting blood flow around the coapting element 34. The balloon 34 provides a more passive rather than user-defined approach to coaptation element shape changing. In one embodiment, the coaptation element 34 has a plurality (e.g. >20) of very thin and highly flexible struts 36 that connect between top and bottom collars, for instance. The struts 36 thus relocate independently of one another, which allows leaflet motion to deform the highly compliant coaptation element 34 into whatever shape best conforms to the remaining orifice. Since segments of the balloon 34 adjacent areas with high leaflet mobility would be compressed, the coaptation element could be dramatically oversized with respect to the regurgitant orifice size in order to maintain coaptation in commissural regions (see FIG. 3D). Since struts on a mechanical balloon stray farther apart when expanded, multiple tubes could be placed within each other at alternating rotation angles in order to increase circularity and strut density.

A locking mechanism is provided on the regurgitation reduction device 30 to lock the position of the coapting element 34 within the tricuspid valve TV and relative to the fixed anchor rail 26. For example, a locking collet 40 along the length of the delivery catheter 32 permits the physician to selectively lock the position of the delivery catheter, and thus the connected coapting element 34, on the anchor rail 26. There are of course a number of ways to lock a catheter over a concentric guide rail, and the application should not be considered limited to the illustrated embodiment. For instance, rather than a locking collet 40, a crimpable section such as a stainless steel tube may be included on the delivery catheter 32 at a location near the skin entry point and spaced apart from the location of the coapting element 34. The physician need only position the coapting element 34 within the leaflets, crimp the catheter 32 onto the anchor rail 26, and then sever both the catheter and rail above the crimp point.

Details of the exemplary locking collet 40 are seen in FIGS. 4A-4C. The collet 40 includes two short tubular grips 42a, 42b that are internally threaded and engage a common externally threaded tubular shaft member 44. The delivery catheter 32 is interrupted by the collet 40, and free ends of the catheter fasten within bores provided in opposite ends of the grips 42a, 42b. As seen in FIG. 4B, the anchor rail 26 extends through the middle of the locking collet 40, thus continuing the length of the delivery catheter 32. Furthermore, when the grips 42a, 42b are separated from each other as seen in FIGS. 4A and 4B, the anchor rail 26 slides freely through the locking collet 40.

An inner, generally tubular wedge member 46 is concentrically positioned between the shaft member 44 and the anchor rail 26. One or both ends of the wedge member 46 has a tapered surface 48 (see FIG. 4C) that interacts with a similarly tapered inner bore of the surrounding tubular grip 42a, 42b. The wedge member 46 features a series of axial slots extending from opposite ends which permit its diameter to be reduced from radially inward forces applied by the surrounding grips 42a, 42b and shaft member 44. More particularly, FIG. 4C shows movement of the two grips 42a, 42b toward each other from screwing them together over the threaded shaft member 44. Desirably, outward ribs or other such frictional enhancers are provided on the exterior of both of the grips 42a, 42b to facilitate the application of torque in the often wet surgical environment. Axial movement of the tapered inner bore of one or both of the grips 42a, 42b forces inward the tapered surface 48 of the wedge member 46, and also the outer ends of the shaft member 44. In other words, screwing the grips 42a, 42b together cams the shaft member and a wedge member 46 inward. The dimensions are such that when the two grips 42a, 42b come together, the inward force applied by the wedge member 46 on the anchor rail 26 is sufficient to lock the delivery catheter 32 and anchor rail.

Now with reference to FIG. 5, the entire regurgitation reduction device 30 can be seen extending from the apex of the right ventricle RV upward through the superior vena cava SVC and into the subclavian vein SV. A proximal length of the delivery catheter 32 including the locking collet 40 exits the subclavian vein SV through a puncture and remains implanted subcutaneously; preferably coiling upon itself as shown. In the procedure, the physician first ensures proper positioning of the coapting element 34 within the tricuspid valve TV, then locks the delivery catheter 32 with respect to the anchor rail 26 by actuating the locking collet 40, and then severs that portion of the delivery catheter 32 that extends proximally from the locking collet. The collet 40 and/or coiled portion of the delivery catheter 32 may be sutured or otherwise anchored in place to subcutaneous tissues outside the subclavian vein SV. It is also worth noting that since the delivery catheter 32 slides with respect to the anchor rail 26, it may be completely removed to withdraw the coapting element 34 and abort the procedure—either during or after implantation. The implant configuration is similar to that practiced when securing a pacemaker with an electrode in the right atrium muscle tissue and the leads extending to the associated pulse generator placed outside the subclavian vein. Indeed, the procedure may be performed in conjunction with the implant of a pacing lead.

FIG. 5A is a schematic diagram of a pair of native tissue leaflets 38 indicating certain key dimensions used in constructing the coapting element. The inquiry seeks to determine a preferred height of the coapting element, or at least the height of the leaflet contacting surface of the elements. It is known that the length of heart valve leaflets are often mismatched, and the dimension LM indicates the leaflet mismatch as a distance along the axis of the valve. An axial dimension of a coapting element that fits within these two mismatched leaflets will therefore have a minimum height that starts at the tip of the longer leaflet and extends upward approximately twice the leaflet mismatch LM dimension, indicated as $H_{min}$. To avoid inserting too large a structure between the leaflets, a dimension $H_{max}$ extends from approximately the plane of the annulus of the leaflets (i.e., where they attach to the surrounding wall) down to a distance into the ventricle which is centered at the center of the dimension $H_{min}$. The leaflet excursion LE reflects the length along which the leaflets are known to contact the coapting devices. That is, the leaflets first hit the device and then move down with the contraction of the heart. There must therefore be enough surface length or leaflet excursion LE for the leaflets to maintain contact. In general, the axial dimension of the coapting element should ensure enough coaptation length to accommodate leaflet mismatch and leaflet excursion without protruding too much into the ventricle or atrium.

Coapting Elements:

As mentioned, a number of different coapting elements are described in the present application. Indeed, the present application provides a plurality of solutions for preventing regurgitation in atrioventricular valves, none of which should be viewed as necessarily more effective than another. For example, the choice of coapting element depends partly on physician preference, partly on anatomical particularities, partly on the results of clinical examination of the condition of the patient, and other factors.

One broad category of coapting element that is disclosed herein and has been subject to testing is a flexible mechanical frame structure at least partially covered with bioprosthetic tissue. The inner frame structure is flexible enough to react to the inward forces imparted by the closing heart valve leaflets, and therefore undergo a shape change to more completely coapt with the leaflets, thus reducing regurgitant jets. The bioprosthetic tissue covering helps reduce material interactions between the native leaflets and the inner mechanical frame. As mentioned above, the regurgitation reduction device can be effectively deployed at either the tricuspid or mitral valves, the former which typically has three leaflet cusps defined around the orifice while the latter has just two. The tissue-covered mechanical balloon thus represents an effective co-optation element for both valves by providing a highly flexible structure which is substantially inert to tissue interactions.

An exemplary embodiment of this so-called "Flexible Bell Coaptation Element" consists of a pericardial tissue (or a biocompatible flexible material) that is cut and sewn to create a sac/bell shape that is able to hold liquid (blood). One embodiment is designed to sit in the valve plane such that the open end is towards the atrium and the closed portion towards the ventricle. Therefore during diastole, blood flows into the coaptation element and fills the sac, conversely during systole as the native leaflets begin to close and contact the coaptation element, the pressure and blood flow work to decrease the size of the coaptation element by pushing blood out of the top edge sufficiently while still creating a seal.

Variations on the system include various design shapes at the ventricular end that is closed such as a half circle, triangle, ellipse or the like. Additionally sutures on the closed end as well as axially along the coaptation element better define how the element closes from interaction with the native leaflets. Lastly a more rigid support such as cloth, wire or other material could be sutured along the open atrial seated edge to ensure that the design remained open during the cardiac cycle. These principles apply equally to coapting elements that are open to the ventricle and closed to the atrium.

For the sake of uniformity, in these figures and others in the application the coapting elements are depicted such that the atrial end is up, while the ventricular end is down. These directions may also be referred to as "proximal" as a synonym for up or the atrial end, and "distal" as a synonym for down or the ventricular end, which are terms relative to the physician's perspective.

FIG. 6A illustrate a coapting element 90 having multiple elongated members, while FIGS. 6B-6C show the tricuspid valve in both diastole and systole, respectively, illustrating the desired coaptation with the leaflets. This coapting element 90 can be viewed in the abstract as a network of elongated "pixels" 92, which can be provided in various forms, such as balloons, rods, tubes, wires, etc. It is advantageous to achieve optimal size, shape, and location of the coaptation element in order to ensure maximal levels of regurgitation reduction in a variety of tricuspid leaflet anatomies. Rather than consisting of one static structure, the coaptation element 90 comprises a network of long, thin balloons 92 of circular cross-section which would each be individually inflatable and deflatable at the time of implant. Thus, the coaptation element could be analogous to a screen of "pixels" with the ability to turn on or off (inflate or deflate) any given pixel to achieve the ideal coaptation element shape, size, and location relative to the valve leaflets. The inflation medium could be designed such that it is fluid at time of implant (in order to inflate/deflate various areas of the device and use echo feedback to determine the optimal combination to reduce TR) but then would cure into a solid or semi-solid within the balloon for long-term stability.

The entire network of balloons 92 in the coaptation element 90 could be covered with a sleeve of pericardium or biocompatible material, with adjustable tension per the "Adjustable Size/Shape Coaptation Element" idea previously discussed. Rather than inflating/deflating individual elements in the balloon network, the cylindrical elements could be added or deleted in any area of the network. For example, a circular "grid" of wires could be constructed, and small cylindrical elements could be advanced through the catheter, into the pericardial coaptation element, and into the specified region where coaptation is lacking. The cylindrical elements could be comprised of a compressible foam or some foam of elastic polymer, such that they would expand when slid distally into the coaptation element and compress when slid proximally into the delivery catheter. This method could be superior to the previously described inflation/deflation method, since maintaining long-term steady pressure in an inflated system could prove to be challenging.

FIGS. 7A/7B show a compressible coapting element 100 with the tricuspid valve in diastole, while FIGS. 8A/8B show the same coapting element and the tricuspid valve in systole. This "hybrid coaptation element" 100 is filled with a deformable fluid so as to have the ability to passively deform its cross-section to a shape that promotes optimal coaptation with the native leaflets. The hybrid solid/fluid coaptation element 100 desirably includes a circular mechanical frame 102 within a larger fluid-filled "sac" 104

(see FIGS. 7A and 7B). The mechanical frame 102 would serve the purpose of occupying the main central regurgitant orifice, while the encompassing fluid-filled sac 104 is deformed by the motion of the leaflets, therefore allowing it to occupy any potential off-center regurgitant orifices in any or all of the three commissural regions between the tricuspid leaflets. The mechanical frame 102 may be comprised of Nitinol struts, while the deformable sac 104 could be made of pericardium or an impermeable bio-inert polymer, and the fluid could be a saline solution. The underlying rigid mechanical frame 102 could be any size or shape other than circular. Also, instead of fluid for the deformable portion of the coaptation element 100, it could be possible to use a highly compressible foam or other elastic polymer. Additionally, this device may be implemented with no internal structure, i.e. struts, but alter its shape with fluid displacement.

Figure 10A:
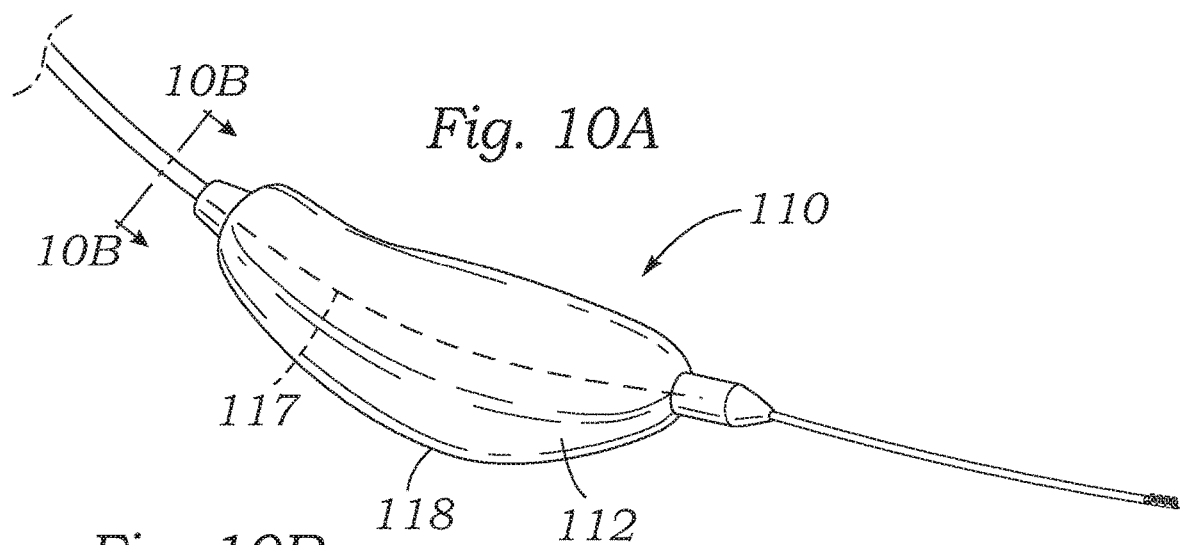
FIGS. 10A and 10B are elevational and end views of the coaptation element from FIGS. 9A-9B.
Figure 10B:
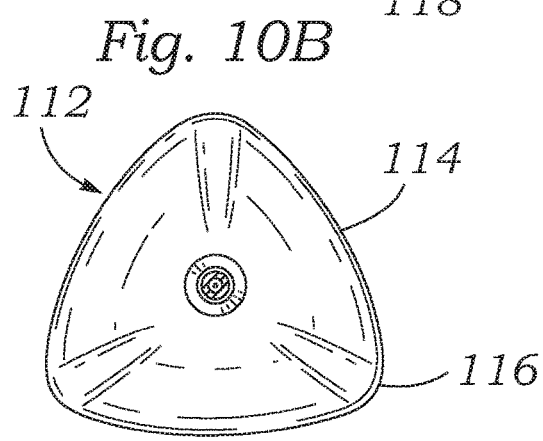

FIGS. 9A-9B illustrate a regurgitation reduction device 110 positioned in the right atrium/right ventricle having a three-sided frame 112 as a coaptation element, and FIGS. 10A and 10B show greater detail of the coaptation element. FIG. 9A shows the heart in diastole during which time venous blood flows into the right ventricle between the open tricuspid valve leaflets and the three-sided frame 112. In the systolic phase, as seen in FIG. 9B, the tricuspid leaflets close around the compressible frame 112, thus coapting against the frame and eliminating openings to prevent regurgitation.

FIG. 10B shows the desirably three-sided radial profile of the frame 112, with three relatively flat convex sides 114 separated by rounded corners 116. This rounded triangular shape is believed to faithfully conform to the three tricuspid leaflets as they close, this better preventing regurgitation. Moreover, the frame 112 is desirably under filled so that it can be compressed and deformed by the leaflets. FIG. 10A also shows a preferred longitudinal profile of the frame 112, with an asymmetric shape having a gradually overall longitudinal curvature 117 and an enlarged belly region 118 just distal from a midline. The shape resembles a jalapeño pepper. Due to the curvature of the path from the superior vena cava SVC down through the tricuspid valve TV and into the right ventricle RV, the overall curvature 117 of the frame 112 helps position a mid-section more perpendicular to the tricuspid valve leaflets, while the uneven longitudinal thickness with the belly region 118 is believed to more effectively coapt with the leaflets.

Figure 11A:
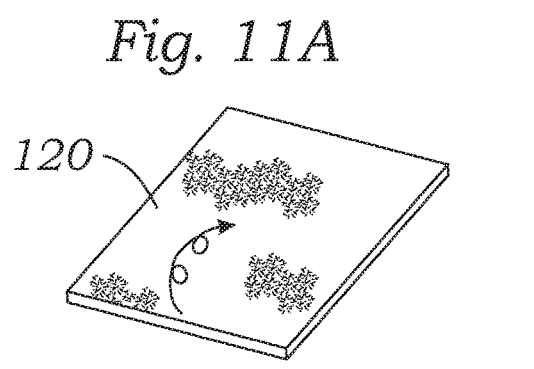
FIG. 11A shows a sheet of bioprosthetic tissue.
Figure 11B:
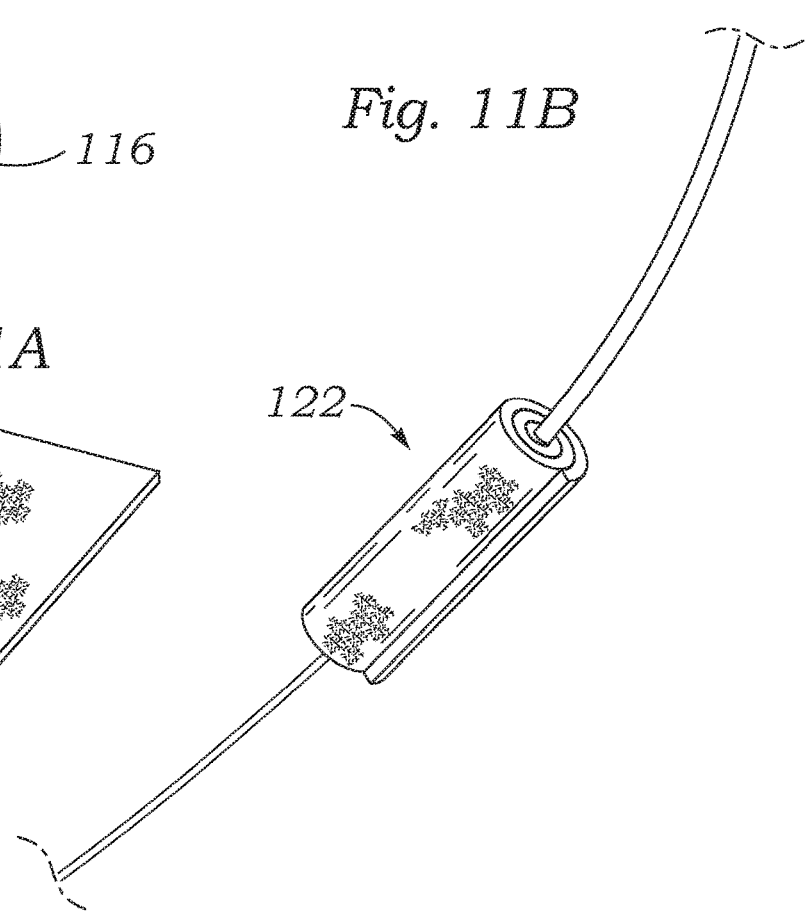
FIG. 11B illustrates a coaptation element formed from rolling the sheet of tissue into a cylinder.

FIG. 11A shows a rectangular sheet 120 of bioprosthetic tissue, and FIG. 11B illustrates a coaptation element 122 formed from rolling the sheet of tissue into a cylinder. This creates a coaptation element 122 with a solid structure and no lumen to fill. Alternatively, if a more compressible structure would be desired for ease of delivery, a relatively softer foam-based material could be used as the structure for the coaptation element, and then a pericardial or other biocompatible material could be used to coat the surface. Multiple different thicknesses of pericardium or a biocompatible polymer (or a combination of the two) could be used to achieve various stiffness levels in the coaptation element. The foam could be used with a biocompatible covering, or the foam could be delivered uncovered, with the intent to promote pannus formation on the device surface, therefore relying on the natural mechanisms of the heart to provide the device with a biocompatible coating.

Adjustable Size/Shape Coaptation Elements:

If the size and/or shape of the coaptation element were to be adjusted in vivo, the surface area of the resulting device would be significantly different than the default situation. Thus, the idea of an adjustable coaptation element supported by a multi-strut mechanical frame, for example, would necessitate independent control of the pericardium or biocompatible covering in order to maintain a taught and smooth coaptation surface. For example, if an equilateral triangular coaptation element were to be adjusted to a much narrower scalene triangle, an independent catheter shaft connected to the proximal end of the biocompatible covering could be pulled, proximally in order to account for the decrease in coaptation element surface area and thus maintain a properly rigid coaptation surface. This concept could be applied with any number of struts greater than two in order to achieve a variety of coaptation element shapes (i.e. ellipse, crescent, acute triangles). Anything between one or all of the mechanical struts could be contained in a rotation channel to alter their orientation around the circumference of the catheter.

Figure 12A:
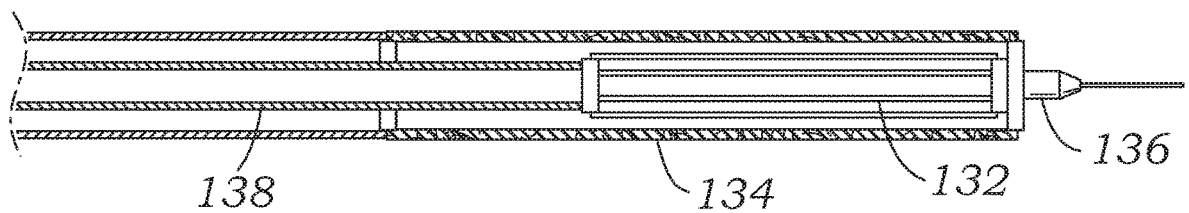
FIGS. 12A-12C are longitudinal sectional views of an "active" coaptation element of the present application forming several different shapes.
Figure 12B:
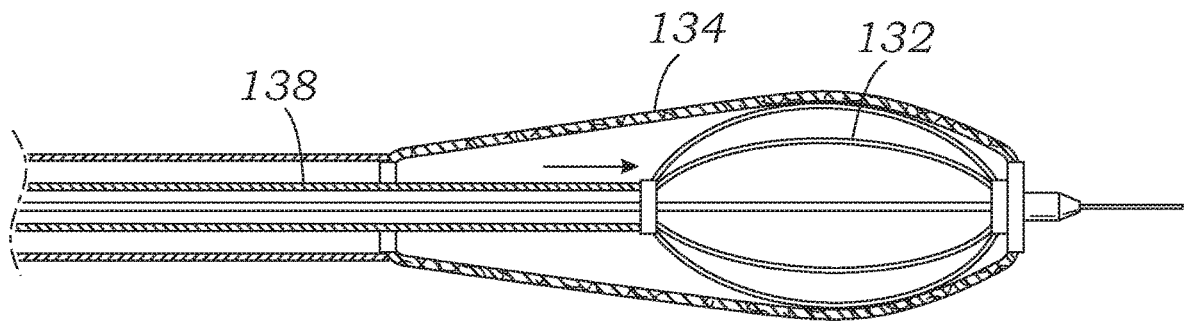
Figure 12C:
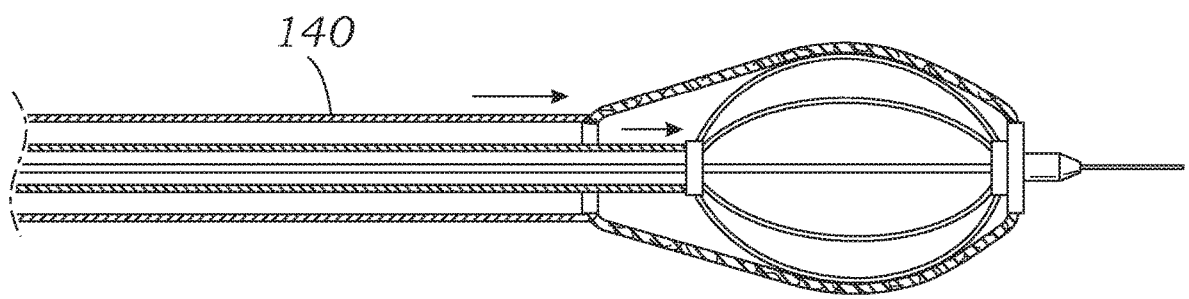

FIGS. 12A-12C are longitudinal sectional views of an "active" coaptation element 130 of the present application forming several different shapes. Given that tricuspid valve anatomy is highly variable between patients in terms of leaflet shapes, sizes, and coaptation surface locations, it could be favorable to develop a coaptation element capable of adjusting shape and size during the implant procedure in order to optimize reduction of tricuspid regurgitation (TR) in a patient-specific manner. An adjustable design feature could be achieved with a "mechanical frame" in which a number of metallic (preferably Nitinol) struts 132 are surrounded by a tube of pericardium 134 or some other bio-inert material, around which the native tricuspid leaflets could coapt and form a seal. The struts 132 would be attached at their distal ends to an inner catheter 136, and at their proximal ends to an adjustable position intermediate catheter 138 which, when pushed distally, causes the mechanical frame struts 132 to bend outward, thus increasing the coaptation element size. An outer catheter 140 to which a proximal end of the tube of pericardium 134 attaches also moves distally from being pulled by outward expansion of the pericardium, as in FIG. 12C. The As for adjustable shape, take the case of a triangular element with three independent struts, for example—if one of these struts were located within a circumferential "channel" within the catheter body around which the strut could be rotated and locked into a new circumferential position, the user could change the shape of the coaptation element from an equilateral triangle to any degree of scalene triangle. This feature could potentially be useful for adjusting the surfaces of the coaptation element to align with the native leaflet anatomy and thus allow for optimal coaptation.

Figure 13A:
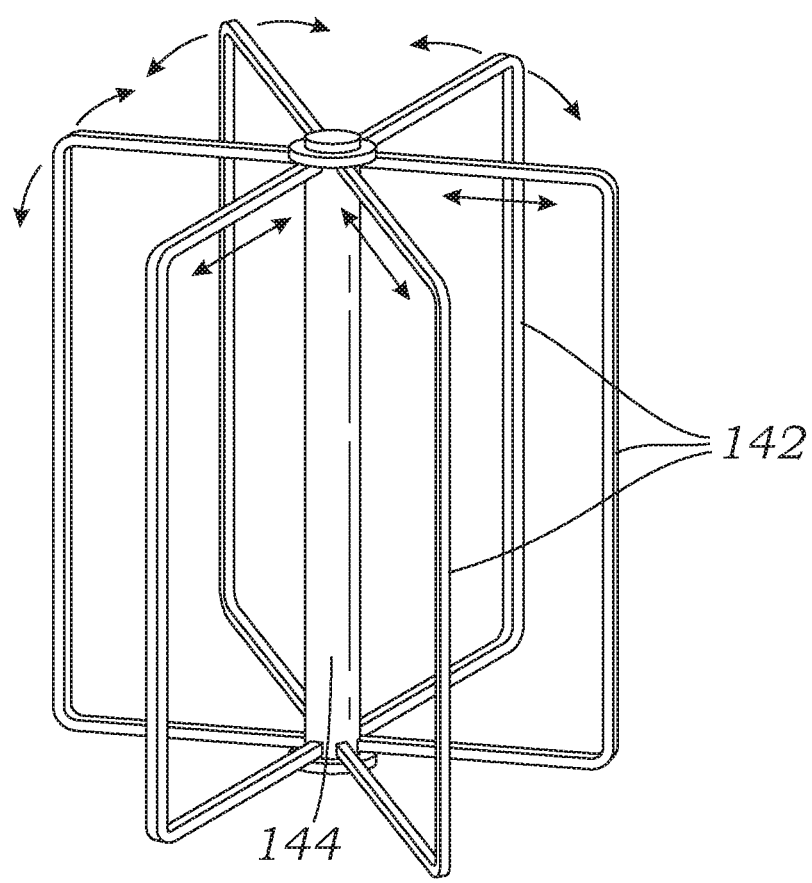
FIGS. 13A and 13B are schematic views of an alternative coaptation element having a plurality of independently rotating rectangular frames which dynamically react to forces exerted thereon by the tricuspid valve leaflets.
Figure 13B:
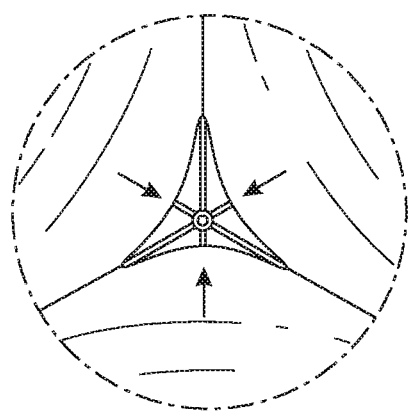

For example, FIGS. 13A and 13B schematically illustrate an aggregation of three rectangular frames 142 that are axially retained with respect to one another and rotational about a catheter or inner hub structure 144. As indicated by the movement arrows, the frames can not only rotate about but can slide linearly along radial lines relative to the inner hub structure 144. Although not shown in the figures, a tissue covering is provided around the frames to act as a barrier preventing inflammation and other deleterious side effects from contact with the material of the frames 142 and the tissue leaflets. The three rectangular structures 142 would have the ability to rotate as well as translate in response to forces from leaflets coapting against the device, thus passively changing shape to shift cross-sectional area of the coaptation element away from portions of the valve with high leaflet mobility and instead to areas with low leaflet mobility and high likelihood of regurgitant jets. The struts 142 may be thin as wire to allow for maximal flexibility and may be oriented in various directions.

FIG. 13B illustrates one possible outcome of interposition of the co-opting element having the frames 142 during diastole when the tricuspid valve leaflets close around the device as well as push the opposite side of the rectangle into a commissure. The independently rotating rectangular frames 142 thus dynamically react to forces exerted thereon by the tricuspid valve leaflets and thus better coapt against the leaflets.

Figure 14A:
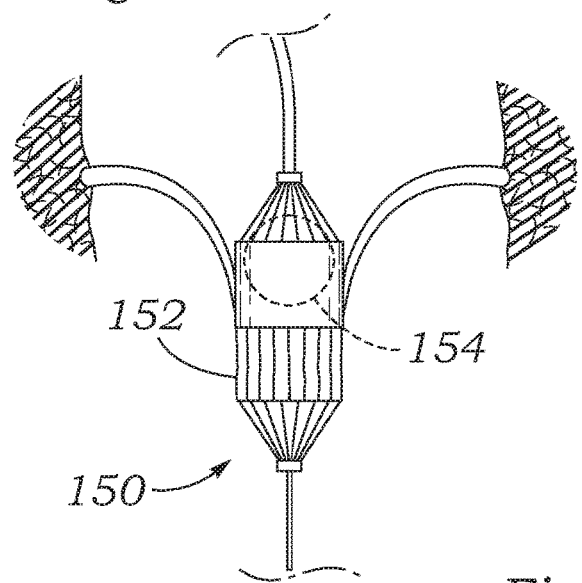
FIGS. 14A/14B and 15 are views of an alternative coapting element having a cage structure and ball valve therein, also showing interaction with the tricuspid valve leaflets.
Figure 14B:
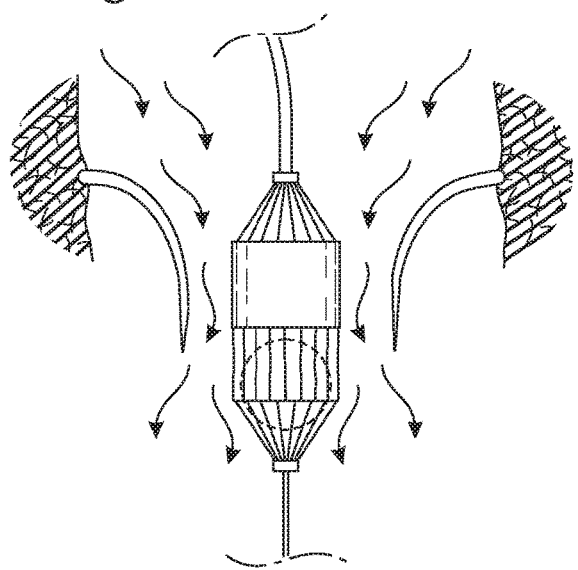
Figure 15:
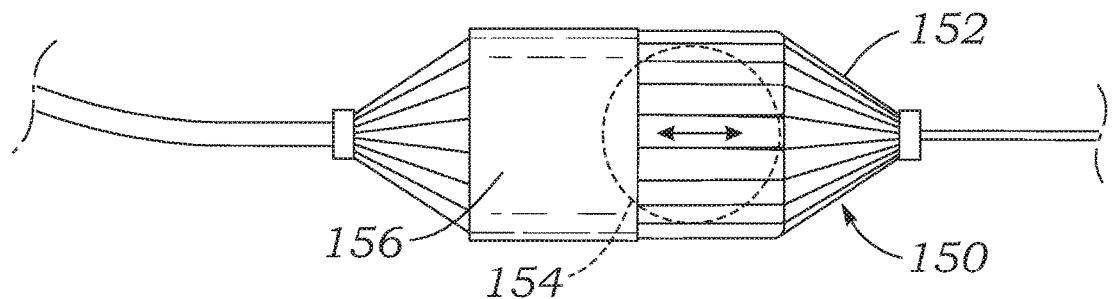

FIGS. 14A/14B and 15 illustrate a coapting element 150 having a cage structure 152 and ball valve 154 therein. The cage 152 may be comprised of structure similar to the previously described mechanical frame, and a bio-inert polymeric ball 154 is housed within the cage. This ball could be compressible (or later expandable) in order to fit through the initial delivery catheter. In order to provide a surface for the leaflets to wrap and form a seal around, an impermeable polymer or other biocompatible surface 156 could be used to cover an upper portion of the cylindrical cage 152 (towards the atrium). During diastole, fluid inertial forces would push the ball 154 down to the ventricular side of the cage, thus allowing flow to pass through the device into the ventricle without any obstruction. During systole, ventricular pressure and fluid inertial forces would push the ball up to the atrial side of the cage into the portion of the cage with the impermeable covering, thus forming a seal to prevent regurgitant flow through the device (the native leaflets wrap against the element to prevent regurgitant flow around the device).

Rather than a ball to seal the inner side of the coaptation element cage 150, a cylindrical plug could be used instead. In this case, it would not necessarily be critical to cover the upper portion of the implant with the impermeable surface 156, since the plug could also function as the surface on which the native leaflets coapt. The cage could be expandable or self-expanding (Nitinol) in order to facilitate passage through a small profile delivery catheter. The polymer ball could be either compressible, inflatable, or expandable at time of implant in order to fit through the same delivery catheter.

Figure 16:
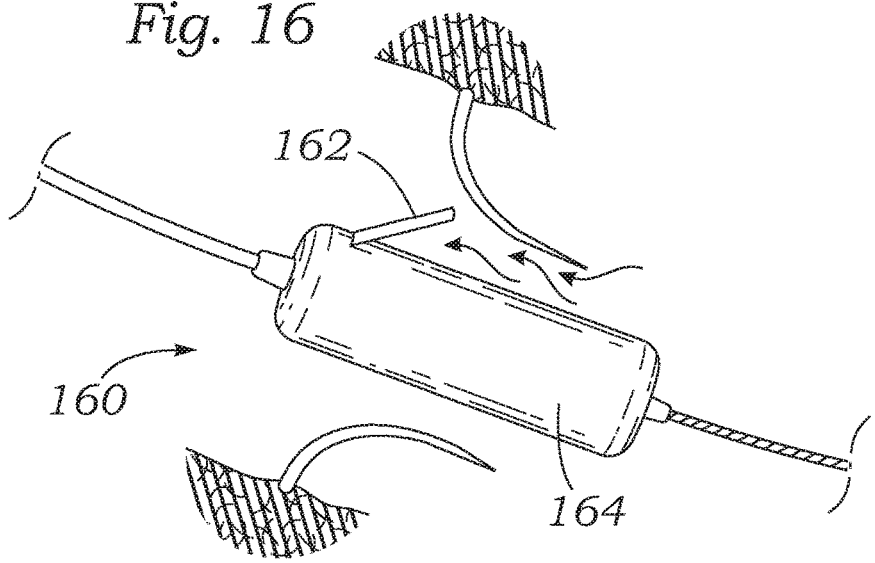
FIG. 16 is a view of another coapting element having a "sail" extending laterally from one side that catches regurgitant flow and adjusts the position of the coapting element.

FIG. 16 is a view of another coapting element 160 having a "sail" 162 extending laterally from one side of an otherwise smooth or cylindrical body 164 that catches regurgitant flow and adjusts the position of the coapting element. The sail 162 could be positioned just on one side, as shown, or around one-quarter or one-half of the device, or any other portion more or less.

Experiments in a bench-top pulsatile flow model with porcine hearts has shown that if the coaptation element 160 is anchored to a non-ideal location in the right ventricle (i.e. at the RV apex close to the anterior or posterior wall), the motion of the native leaflets cannot always self-center the coaptation element towards the expected central location of the regurgitant orifice. If the coaptation element gets stuck in a non-central location, higher levels of TR can be expected. Aside from ensuring central anchor location, one potential way to address this issue could be to equip the coaptation element with a series of individually adjustable "flaps" or "sails" around its circumference which in the default state would lie flat along the coaptation element, but could each be deployed on a hinge to catch systolic fluid flow in the RV and therefore pull the coaptation element in a particular direction, such as to a central position. The series of flaps could each be tested to determine which is in the correct location to induce systolic movement of the coaptation element towards the annulus center. Any number of sails or flaps could be used, preferably greater than two. The hinge point could be at the proximal end of the sail, such that it deploys upwards, or at the distal end of the sail, such that it deploys downwards.

Figure 17A:
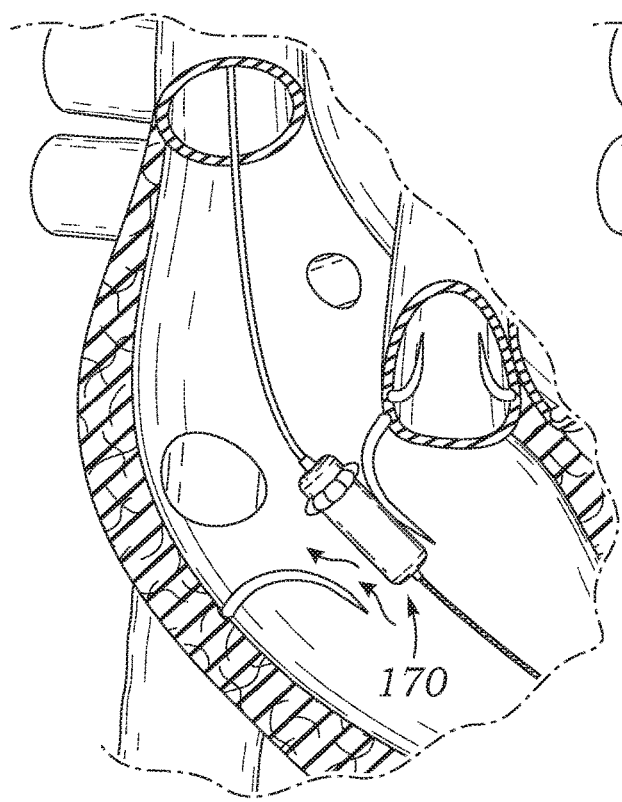
FIGS. 17A and 17B are views of a coapting element having a circumferential skirt extending outward therefrom positioned within the tricuspid valve leaflets.
Figure 17B:
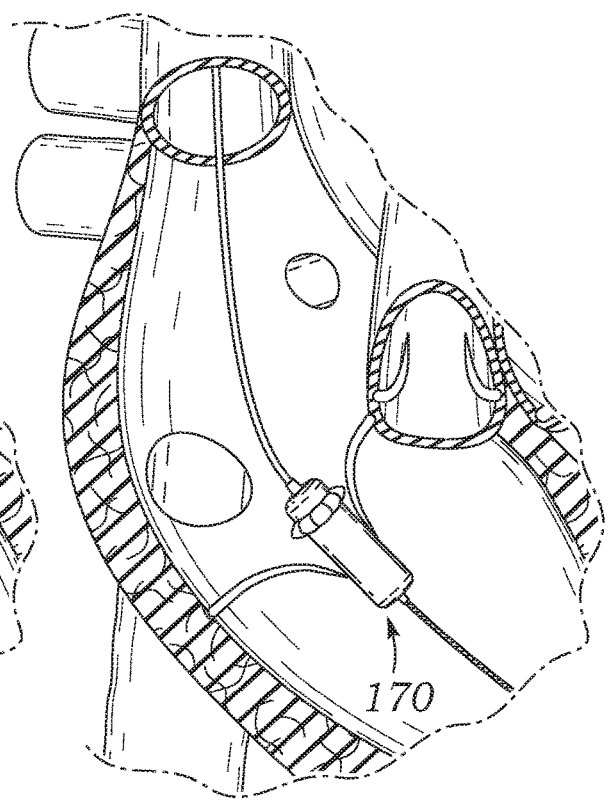
Figure 18A:
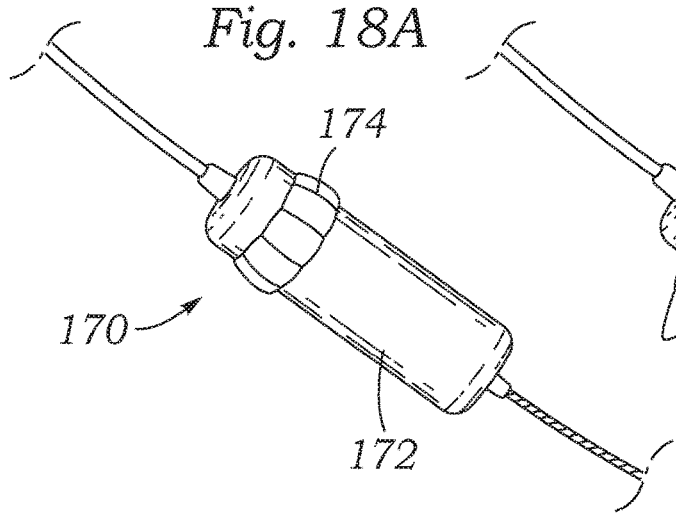
FIGS. 18A-18B are enlarged views of the coapting element with the skirt contracted and expanded, respectively.
Figure 18B:
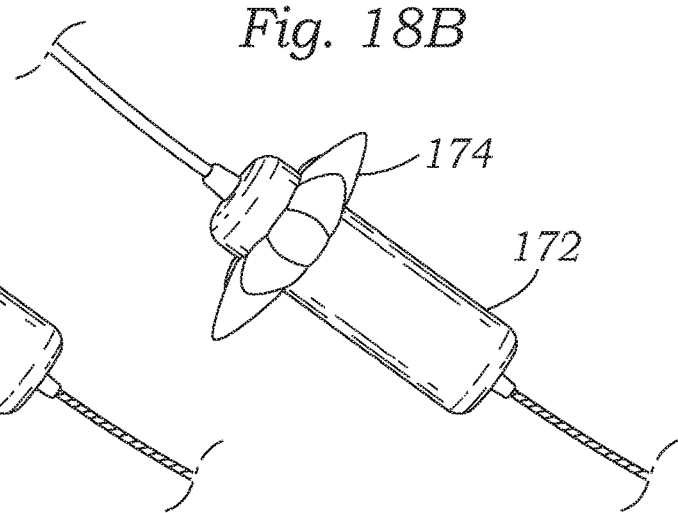

FIGS. 17A and 17B are views of a self-centering coapting element 170 that adjusts to regurgitation by laterally adjusting position. FIGS. 18A-18B illustrate the coapting element 170 with a generally smooth or cylindrical body 172 and a circumferential skirt 174 shown contracted and expanded, respectively. As with the sails discussed above, the skirt 174 normally remains bias against the cylindrical body 172 (or other shape), and all or a portion thereof pivots outward when caught by regurgitant flow to move the coapting element 170 toward that flow, such as to a central position. In this way, the coapting element 170 dynamically reacts to fluctuating fluid flows around the device to move in desired directions to close the regurgitant flow.

Figure 19B:
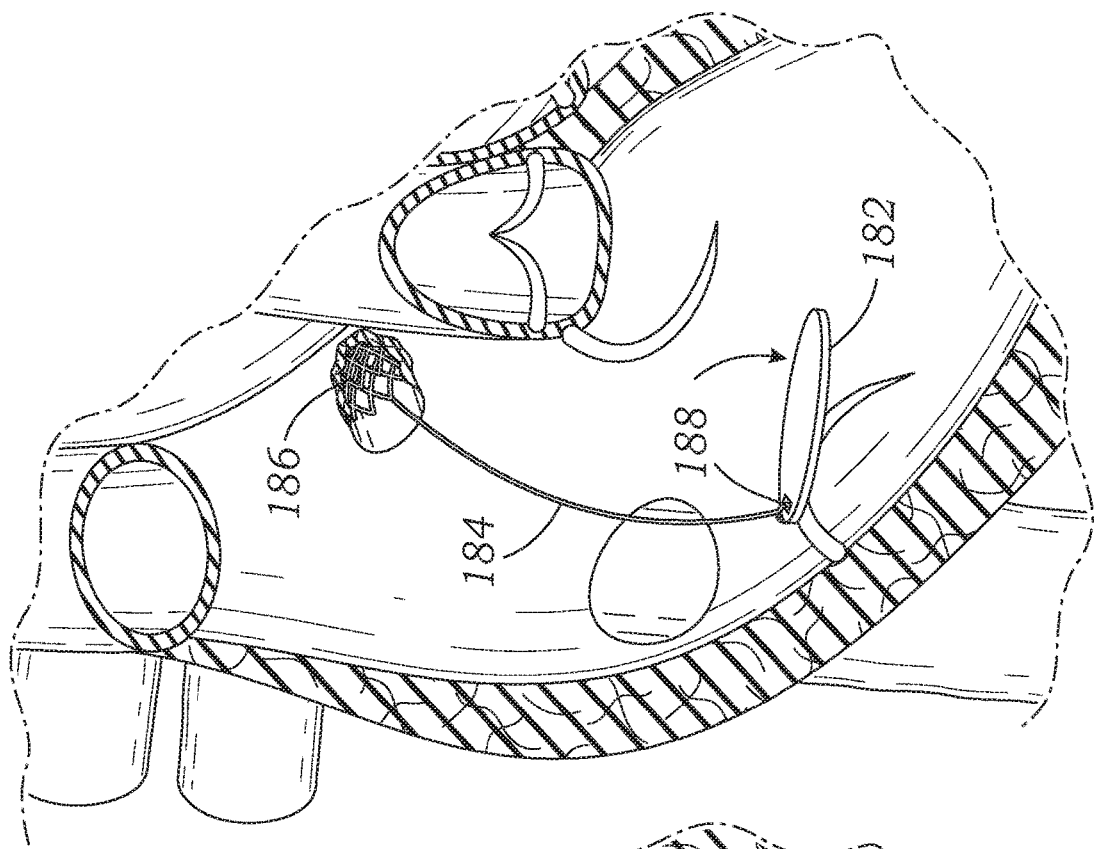
FIGS. 19A and 19B show an alternative regurgitation reduction device having a flapper valve that interacts with the tricuspid valve leaflets and is anchored by a stent within a coronary sinus opening to the right atrium.
Figure 19A:
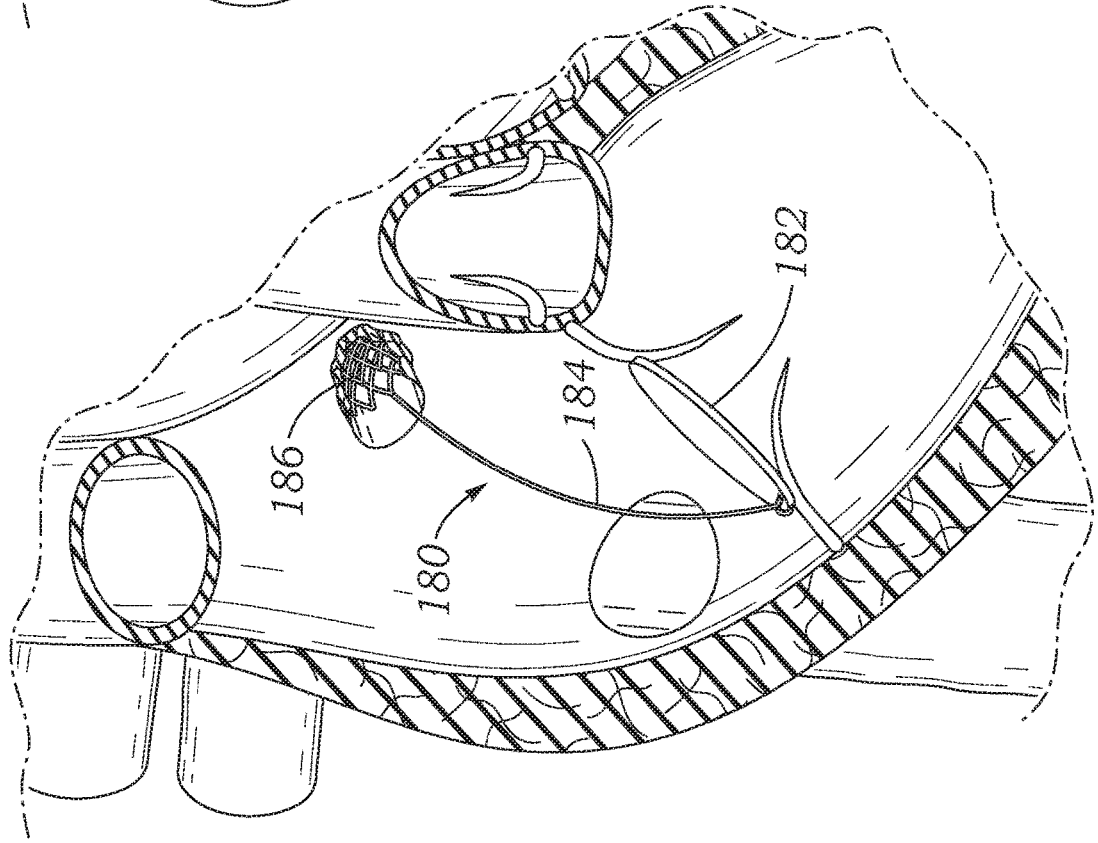

FIGS. 19A and 19B show a still further regurgitation reduction device 180 including a flapper valve 182 that interacts with the tricuspid valve leaflets. The flapper valve 182 is anchored by a tether 184 to a stent 186 pre-positioned within a coronary sinus opening to the right atrium. Rather than occupying the regurgitant orifice with a long cylindrical device, the coaptation surface is formed generally across the tricuspid valve by the circular disk or coaptation "lid" 182 (essentially a cylinder but with negligible length). The disk 182 could be a metallic structure covered with pericardium or a bio-inert polymer such as silicone, and it is desirably anchored in place via the connecting member 184 and cylindrical stent 186. In order to minimize restriction of flow during diastole, the disk could be mounted on a hinge mechanism 188 such that it would hinge downwards (to align vertically) during diastole and hinge upwards (to align horizontally) during systole. A hinge feature could allow for significant oversizing of the disk with respect to the regurgitant orifice area, thus ensuring proper coaptation from the leaflets even if further RV remodeling and annular dilatation were to occur. Rather than anchoring the lid element in the coronary sinus, it could be anchored via a shaft to the RV apex, or alternatively from the superior vena cava.

FIGS. 20A and 20B show a tricuspid valve interacting with a regurgitation reduction device 190 having a coil-spring coapting element 192 anchored via a tether 194 to a stent 196 within a coronary sinus. When subject to diastolic flow, as in FIG. 20B, the coil-spring coapting element 192 would expand downwards towards the RV apex and therefore allow flow through the spring. During systole, as in FIG. 20A, the coil-spring coapting element 192 compress from a conical spring into a flat disk, similar to the previously described embodiment.

Figure 21A:
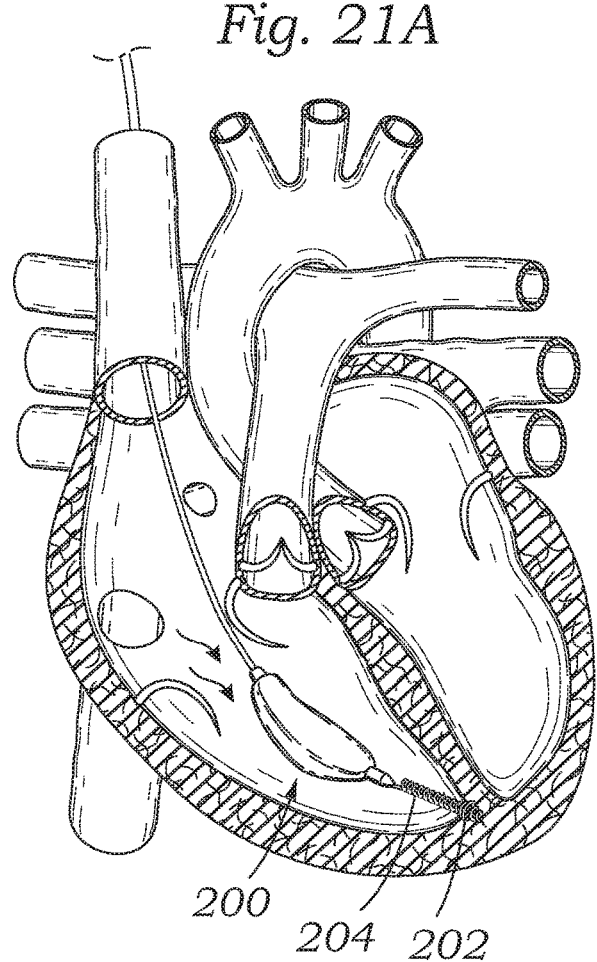
FIGS. 21A and 21B are sectional views of the heart in diastole and systole, respectively, showing a regurgitation reduction device which is mounted to the apex of the right ventricle with a spring that permits a coapting element to move in and out of the right ventricle in accordance with the cardiac cycle.
Figure 21B:
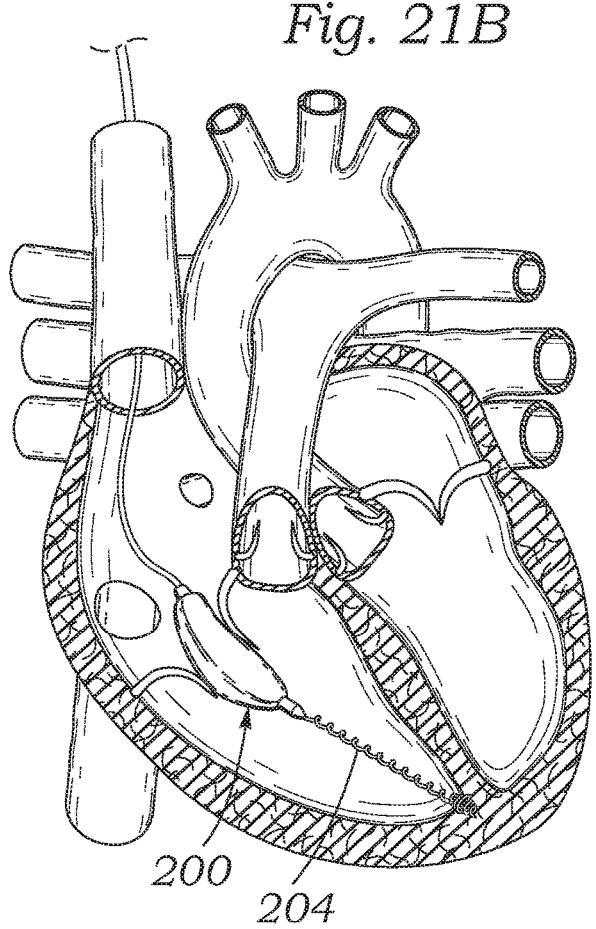

One potential challenge of a static coaptation element within the tricuspid valve annulus could be diastolic stenosis, i.e. restriction of blood flow from the right atrium to the right ventricle during diastole. In patients with an excessively large regurgitant orifice, sizing the device for proper coaptation during systole could have consequences in diastole. To address this issue, a coaptation element 200 could be attached to a flexible metallic spring 204 connected to anchor 202, therefore allowing the coaptation element to move in and out of the annulus plane during systole and diastole, respectively (see FIGS. 21A and 21B). During systole, as in FIG. 21B, the pressure gradient as well as fluid inertial forces would cause the spring 204 to extend, and during diastole the spring constant as well as fluid inertial forces would cause the spring to contract. Instead of just one spring distal to the coaptation element, a spring could be placed on both sides in order to increase mobility. Alternatively, with one spring, the "home" position of the coaptation element (i.e. with no force from the spring or fluid) could either be at the annulus plane or below the annulus plane in the RV. In the former case, inertial forces of diastolic flow would be required to move the coaptation element down out of the annulus plane during diastole, and in the latter case, both inertial forces of systolic flow and forces from the RV/RA pressure gradient could move the coaptation element up to the annulus during systole.

Figure 22:
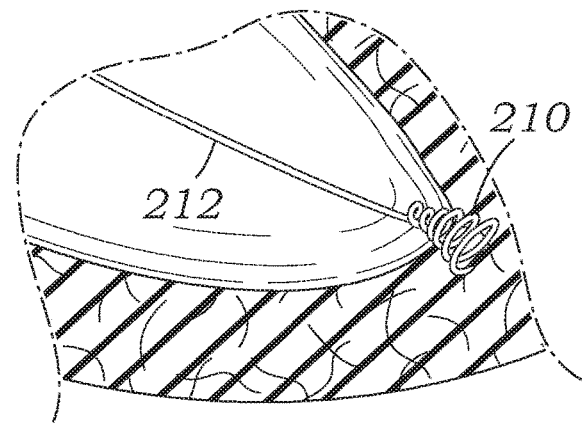
FIGS. 22 and 23 are views of alternative anchoring members utilizing coil springs.
Figure 23:
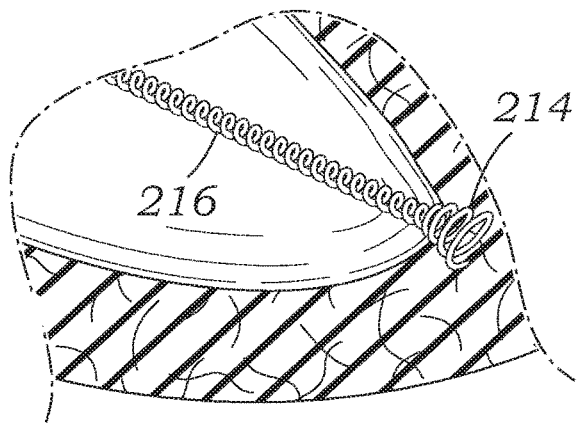

Anchors and Alternative Anchor Placement:

The following list of embodiments presents additional design ideas for the catheter railing and anchoring system:

FIGS. 22 and 23 are views of alternative anchoring members utilizing conical coil springs. One potential challenge of some proposed helical anchors is the limited surface area on which the anchor can "grab" tissue given its short cylindrical length (2 mm). In order to maximize the area of tissue contact over the 2 mm length of the anchor, a modified helical anchor 210 could be developed which has a conical shape, i.e. a circular cross-section of increasing size towards the distal end. The conical spring anchor 210 could be provide at the end of an anchor rail 212, as previously described. Such an anchor design could increase retention force by increasing the cross-sectional area of contact between the anchor coil and the tissue. Additionally, as the initial cut of the anchor 210 into the tissue would be largest followed by decreasing coil diameter as the anchor is screwed in, the anchor could effectively "cinch" in a volume of tissue into a compacted space. Such a feature could potentially minimize the risk for anchor tear-out by increasing the local tissue density at the anchor site. The conical spring 210 could be comprised of any shape memory material capable of collapsing or wrapping down to a smaller constant diameter to fit through a catheter lumen, then capable of expanding to the natural conical shape upon exiting the delivery sheath into the RV.

Alternatively, a conical anchor 214 could be connected via an elongated helical section 216 at its proximal end designed to remain in the RV (not screwed into the tissue but directly next to it), such as shown in FIG. 23. The elongated helical section 216 provides shock absorption capabilities against compressive/tensile stresses, thus reducing tear-away stresses on the RV apex, and also flexibility capabilities under bending stresses.

Figure 24:
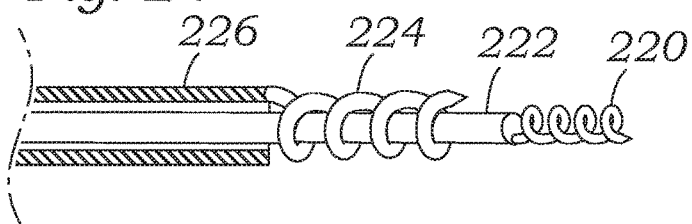
Figure 24A:
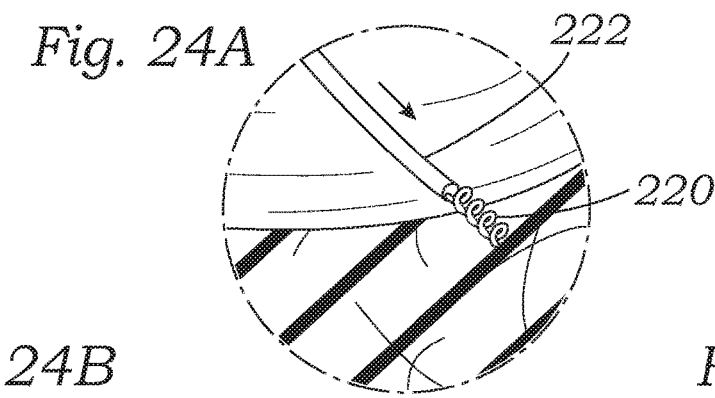
FIGS. 24A-24C illustrate steps in installation of the anchoring device.
Figure 24B:
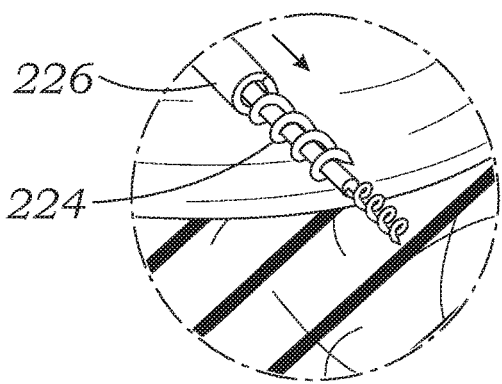
Figure 24C:
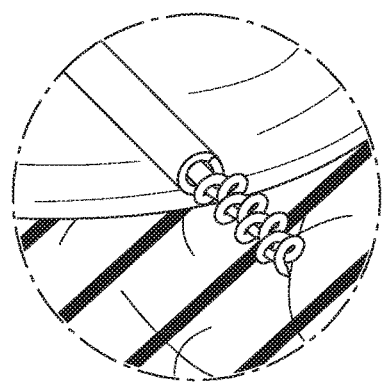

Using helical structures for anchoring the devices described herein in the right ventricle holds a number of advantages (e.g. ease of delivery, acute removability, minimal tissue damage, etc.). However, one potential challenge could be the tendency of a helical structure to "unscrew" itself out of the tissue, either acutely or over time due to the contractile motions of the ventricle. To address this issue, an anchor system in FIG. 24 includes concentric corkscrew anchors; an inner anchor 220 at the end of an inner tube 222, and an outer anchor 224 on the end of an outer tube 226. FIGS. 24A-24C illustrate steps in installation of the anchoring device, in which first the inner anchor 220 having a clockwise orientation is screwed into the tissue. Next, the slightly larger second anchor 224, having a counterclockwise orientation, and its tube 226 slide over the first anchor 220 and tube 222 and screws into the tissue in the opposite direction. Finally, the two anchors could be fixed together with a locking mechanism (e.g., pin-through-hole style). The resulting structure would resist unscrewing out of the tissue, since each helical coil opposes the twisting motion of the other.

Figure 25:
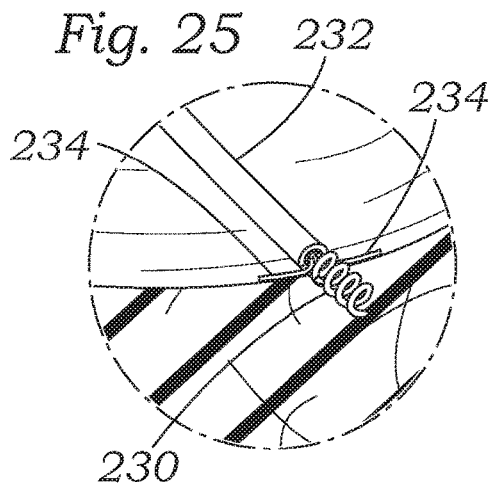
FIGS. 25 and 26 are views of still further anchoring members of the present application.

FIG. 25 shows another configuration with a helical corkscrew-type anchor 230 on the end of a tube 232, and a pair of struts 234 that may be independently expelled from the distal end of the tube into contact with the tissue surrounding the anchor. Rather than screwing in a second relatively similar anchor in the opposite direction to prevent twist-out, the struts 234 pass through the tube lumen and extend outwards in an L-shaped manner to provide an anti-rotation anchor to the device. These struts 234 should be thick enough to press against the RV apex tissue and apply friction thereto to prevent twisting motion of the anchor 230.

Figure 26:
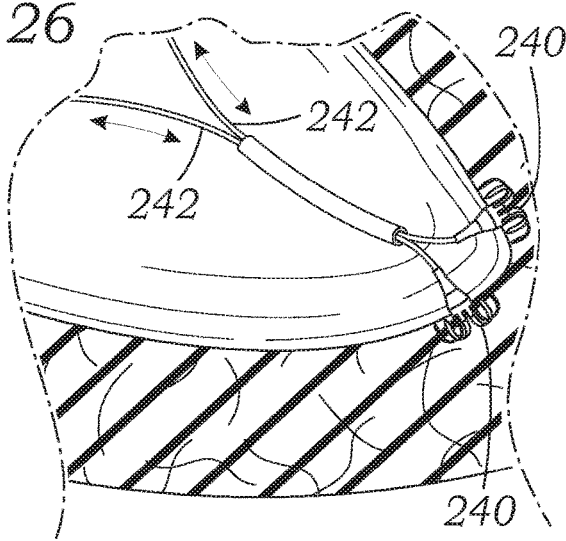

In an alternative approach to enabling fine control over the position of the coaptation element within the valve plane, as seen in FIG. 26, a series of two or more anchors 240 could be deployed in various areas of the RV (including possibly the papillary muscles). The attached anchor rails 242 could all extend through a lumen of the coaptation element (not shown). In order to re-position the coaptation element, the tension on any given anchor rail 242 could be altered independently at the access site, thus increasing or decreasing the degree of tethering on the coaptation element in a certain direction. For example, to move the coaptation element to a more posterior position within the valve, the anchor rail 242 corresponding to the more posterior anchor 240 could be pulled more taught. Once the desired position is achieved, the relative lengths of all the anchor rails could be fixed with respect to the coaptation element catheter via a locking or clamping mechanism at the proximal end of the device. The anchor rails referenced previously could instead be cable wires (with no lumen) in order to minimize the profile of the coaptation element catheter given that multiple anchor attachments will need to fit within the device inner lumen. In order to facilitate easily distinguishing which cable attaches to which anchor, the catheter could contain a series of lumens (at least two) for cable wires which would be labeled based on anatomical location of the corresponding anchor. Therefore, at the proximal end of the device, it would be clear which cable would be required to pull in order to translate the coaptation element in a certain direction.

FIGS. 27A and 27B show operation of a centering balloon 250 that helps ensure proper positioning of an anchor 252 at the apex of the right ventricle. A series of experiments in a bench-top pulsatile flow model with porcine hearts has emphasized the importance of RV anchor position for achieving central location of the coaptation element within the valve. Thus, it may be necessary to utilize an accessory catheter 254 for the present device to help facilitate delivery of the anchor 252 to the ideal location within the ventricle, or the centering balloon 250 may be mounted on the distal end of the delivery/anchoring catheter itself. One such approach relies on using the annulus itself to guide the anchor shaft. For instance, a perfusion balloon 250 large enough to fill the entire valve could be inflated within the tricuspid annulus, therefore counting on opposition between the annulus and the perfusion balloon to orient the angle of the catheter lumen directly normal to and through the center of the valve plane. FIG. 27A shows the unwanted position of the anchor 250 before balloon inflation, while FIG. 27B shows the desired positioning at the RV apex after the balloon 250 is inflated. At this point, the anchor shaft would pass through the lumen of the perfusion balloon catheter (either an accessory catheter or the delivery catheter itself), which is oriented so as to guide the anchor to the ideal central location along the anterior-posterior axis of the RV apex. The centering balloon 250 allows the delivery system to track into the RV while avoiding chords and ensuring central placement rather than between leaflets.

Figure 28:
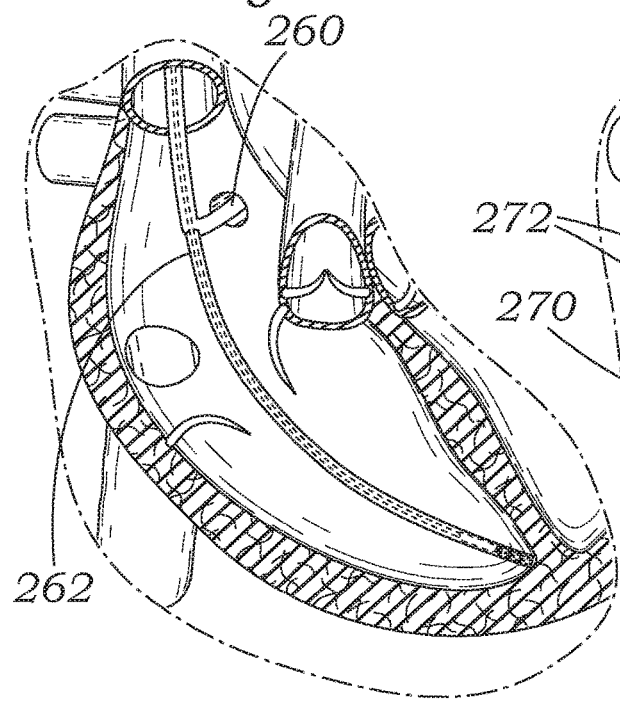
FIG. 28 illustrates a step in directing an anchoring catheter to the apex of the right ventricle using an L-shaped stabilizing catheter secured within a coronary sinus.

FIG. 28 illustrates a step in directing an anchoring catheter 260 to the apex of the right ventricle using an L-shaped stabilizing catheter 262 secured within a coronary sinus. This configuration addresses the challenge of guiding the anchor delivery. The catheter 262 is capable of deflecting into an L-shape, and would be advanced from the SVC, into the right atrium, then into the coronary sinus, which would provide a stabilizing feature for the guide catheter that is within a direct line to the tricuspid annulus. The catheter 262 could be maneuvered further in or out of the coronary sinus such that the "elbow" of the L-shape is positioned directly above the center of the valve, then the anchor catheter 260 could be delivered through the lumen of the guide catheter 262 and out a port at the elbow of the L-shape. A temporary stiffening "stylet" (not shown) could be used through the anchor rail lumen to ensure the anchor is delivered directly downwards to the ideal point at the RV apex.

Figure 29:
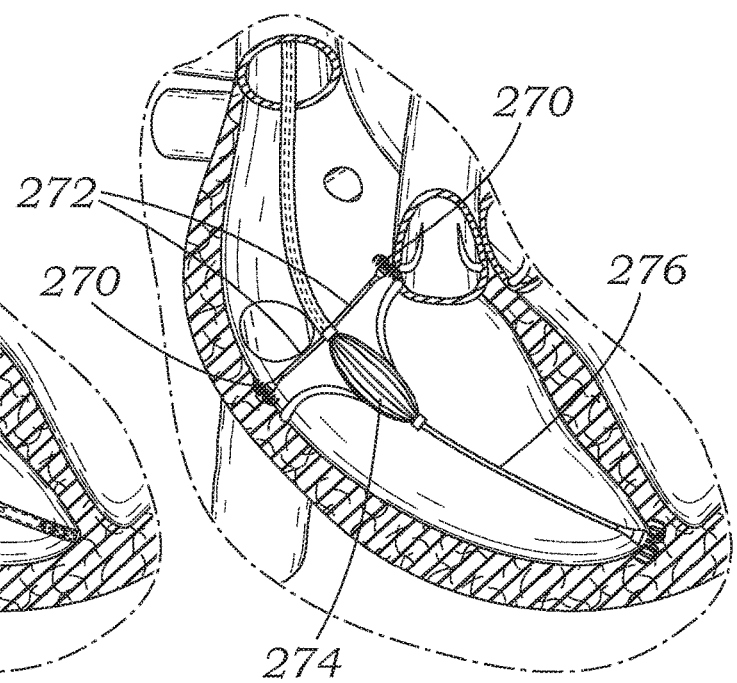
FIG. 29 schematically illustrates a stabilizing rod extending laterally from a regurgitation reduction device delivery catheter in the right atrium above the tricuspid valve.

If any of the previously described anchoring options involving any combination of the RV, SVC, and IVC prove to be undesirable, the coaptation element could instead be anchored directly to the annulus. As shown in FIG. 29, a series of at least two anchors 270 (similar to the helical RV anchors) could be deployed into the fibrous portion of the annulus, then cables or stabilizing rods 272 could be used to hang or suspend the coaptation element 274 within the annulus plane. Each support cable or rod 272 would need to be relatively taught, so as to prevent motion of the device towards the atrium during systole. Any number of supports struts greater than two could be utilized. The support cables for suspending the coaptation element from the annulus could be relatively flexible, and thus the position and mobility of the device would be altered via tension in the cables. Alternatively, the support elements could be relatively stiff to decrease device motion, but this would require changing anchor position to reposition the coaptation element. Although an anchor 276 to the RV apex is shown, the dual annulus anchors 270 might obviate the need for a ventricular anchor.

Figure 30:
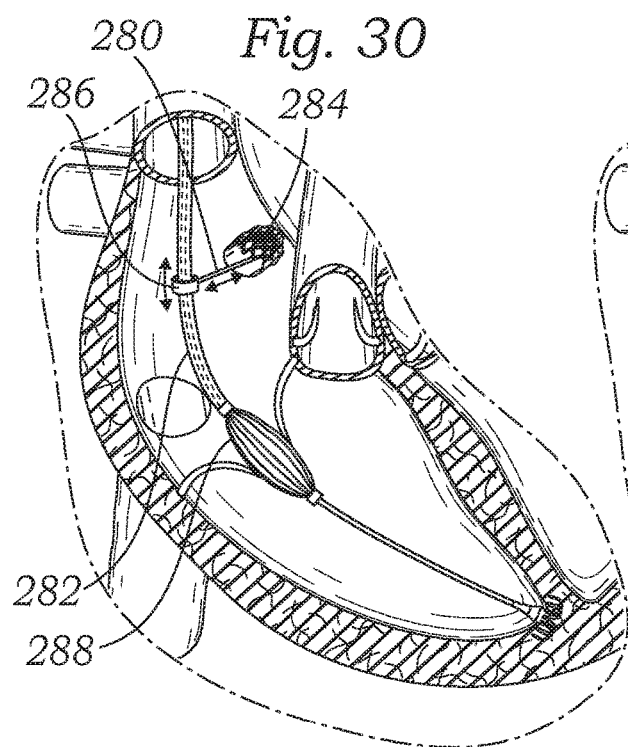
FIG. 30 illustrates an adjustable stabilizing rod mounted on the delivery catheter and secured within the coronary sinus.

The general concept of cylindrical stent-based anchor mechanisms for the device could be applied in other structures near the tricuspid valve such as the coronary sinus. For instance, FIG. 30 illustrates an adjustable stabilizing rod 280 mounted on a delivery catheter 282 and secured to an anchor 284 within the coronary sinus. The stabilizing rod 280 attaches via an adjustable sleeve 286 to the catheter 282, thus suspending the attached coapting element 288 down into the regurgitant orifice. A sliding mechanism on the adjustable sleeve 286 permits adjustment of the length between the coronary sinus anchor 284 and the coaptation device 288, thus allowing positioning of the coaptation element at the ideal location within the valve plane. Once again, the securing and adjustment mechanism 284, 286 are within a direct line to the tricuspid annulus so as to facilitate positional adjustment thereof. For further stability, this coronary sinus anchoring concept could also be coupled with a traditional anchor in the RV apex, as shown.

Figure 31:
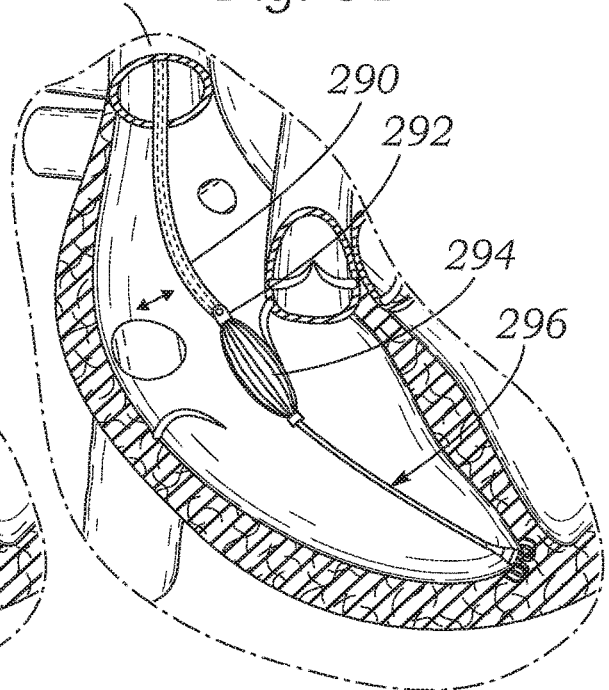
FIG. 31 illustrates an alternative delivery catheter having a pivot joint just above the coapting element.

While venous access to the RV through the subclavian vein and into the superior vena cava is a routine procedure with minimal risk for complications, the fairly flat access angle of the SVC with respect to the tricuspid valve plane presents a number of challenges for proper orientation of the present coaptation element within the valve. If the catheter were not flexible enough to achieve the correct angle of the coaptation element with respect to the valve plane by purely passive bending, a flex point could be added to the catheter directly proximal to the coaptation element via a pull wire attached to a proximal handle through a double lumen extrusion. For instance, FIG. 31 illustrates an alternative delivery catheter 290 having a pivot joint 292 just above the coapting element 294 for angle adjustment. If a given combination of SVC access angle and/or RV anchor position resulted in a crooked coaptation element within the valve plane, the catheter 290 could be articulated using the pull wire (not shown) until proper alignment is achieved based on feedback from fluoroscopic views.

Additional flex points could be added to further facilitate control of device angle, e.g. another flex point could be added distal to the coaptation element 294 to compensate for the possible case that the RV wall angle (and thus the anchor angle) is skewed with respect to the valve plane. This would require an additional independent lumen within the catheter body 290 to facilitate translation of another pull wire to operate the second flex feature. Alternatively, if a single flex point proximal to the coaptation element were determined to be sufficient for orienting the device, and if the catheter were rigid enough to resist the forces of systolic flow, the section 296 of the device distal to the coaptation element could be removed all together. This would leave only one anchoring point for the device in the SVC or subcutaneously to the subclavian vein. Also, as an alternative to an actively-controlled flex point, the catheter could contain a shape-set shaft comprised of Nitinol or another shape memory material, which would be released from a rigid delivery sheath into its "shaped" form in order to optimize device angle from the SVC. It could be possible to have a few catheter options of varying pre-set angles, yet choose only one after evaluation of the SVC-to-valve plane angle via angiographic images.

Instead of using an active mechanism within the catheter itself to change its angle, another embodiment takes advantage of the surrounding anatomy, i.e. the SVC wall. FIGS. 32A and 32B show two ways to anchor the delivery catheter 300 to the superior vena cava SVC for stabilizing a coapting element 302. For example, a variety of hooks or anchors 304 could extend from a second lumen within the catheter 302 with the ability to grab onto the SVC wall and pull the catheter in that direction (FIGS. 32A and 32B). Alternatively, a stiffer element could extend outwards perpendicular to the catheter axis to butt up against the SVC wall and push the catheter in the opposite direction. The SVC is within a direct line to the tricuspid annulus, thus rendering relatively easy the adjustment of the coapting element 302. For especially challenging SVC geometries, such a mechanism could potentially be useful for achieving better coaxial alignment with the valve.

FIGS. 33A and 33B show an active regurgitation reduction device 310 having pull wires 312 extending through the delivery catheter 314 for altering the position of the coapting element 316 within the tricuspid valve leaflets. If the coapting element 316 is located out of the middle of the valve leaflets such that it does not effectively plug any regurgitant jets, which can be seen on echocardiography, then one of the pull wires 312 can be shortened or lengthened in conjunction with rotating the catheter 314 to reposition the coapting element 316, such as seen from FIG. 33A to FIG. 33B.

Although pacemaker leads are frequently anchored in the right ventricle with chronic success, the anchor for the present device would see significantly higher cyclic loads due to systolic pressure acting on the coaptation element. Given that the right ventricle wall can be as thin as two millimeters near the apex and the tissue is often highly friable in patients with heart disease, anchoring a device in the ventricle may not be ideal. An alternative anchoring approach could take advantage of the fairy collinear orientation of the superior and inferior vena cava, wherein, as seen in FIG. 34, two stent structures 320, 322 would effectively "straddle" the tricuspid valve by expanding one in the superior vena cava and the other in the inferior vena cava. The coaptation element 324 would then hang down through the tricuspid valve plane from an atrial shaft 326 attached to a connecting wire or rod 328 between the two caval stents 320, 322. In order to resist motion of the coaptation element under systolic forces, the shaft 326 from which the coaptation element 324 hangs would be fairly rigid under compressive and bending stresses. The coaptation element 324 would desirably be positioned within the valve using a sliding mechanism along the connecting rod 328 between the two caval stents. Once again, the direct access to the tricuspid annulus provided by the connecting rod 328 between the two caval stents greatly enhances the ability to easily position the coaptation element 324.

The coaxial orientation of the SVC and IVC could also be leveraged for delivering an anchor into the RV. A delivery catheter could be passed through the SVC into the IVC, and a "port" or hole off the side of the delivery catheter could be aligned with the center of the valve. At this point, the anchor could be passed through the lumen of the delivery system and out the port, resulting in a direct shot through the center of the annulus and to the RV wall in the ideal central anchor location.

This concept could potentially be applied to the left side of the heart as well, to address mitral regurgitation. A coaptation element could reside between the mitral valve leaflets with anchors on both the proximal and distal ends: one attaching to the septal wall, and the other anchoring in the left atrial appendage. The septal anchor could be a helical or hook-style anchor, whereas the left atrial appendage anchor could be an expandable metallic structure with a plurality of struts or wireforms designed to oppose against the appendage wall and provide stability to the coaptation element.

Pacemaker leads frequently lead to tricuspid regurgitation (TR) by pinning a leaflet or interfering with leaflet mobility. In this particular embodiment, a device, a gap filler, is designed to be introduced over the offending pacemaker lead (of course, applicable also to those with organic tricuspid regurgitation and a pacemaker lead in place). The invention is a tricuspid regurgitant volume gap filler that is placed over the existing pacemaker lead via a coil wound over the lead or a slit sheath approach, which acts like a monorail catheter. The gap filler catheter is advanced over the pacemaker lead and the tricuspid regurgitation is evaluated by echo while the monorail gap filler device is placed into the regurgitant orifice. The proximal end of the gap filler allows for crimping and truncating the catheter post-balloon inflation or gap filler deployment. This mates the monorail gap filler to the pacemaker lead at the proper position within the tricuspid valve.

FIGS. 35-36 are schematic views of a coapting element 330 mounted for lateral movement on a flexible delivery catheter 332 that features controlled buckling. It is challenging to reposition the coaptation element 330 from an off-center location to the ideal central location within the valve plane, given a fixed angle from the SVC and a fixed anchor position in the RV. The device catheter 332 could be comprised of a fairly stiff shaft except for two relatively flexible regions 334, 336 directly proximal and distal to the coaptation element section. The farthest distal section of the coaptation catheter 332 could be locked down relative to the anchor rail over which it slides, and then the catheter 332 could be advanced distally thus compressing it and causing the two flexible sections 334, 336 to buckle outwards and displace the coaptation element laterally with respect to the catheter axis (see FIG. 35C). At this point, the user could employ a combination of sliding and rotating of the catheter to reposition the coaptation element 330 within the valve using short-axis echo feedback. Instead of locking the distal end of the catheter onto an anchor rail before adjustment, if the catheter were comprised of multiple lumens, the outer lumen could slide distally relative to the inner lumen, thus producing the same buckling effect.

In another embodiment, not shown, an alternative approach could be to rely on the contractile motion of the heart to move a tapered coaptation element in and out of the tricuspid valve plane. A tapered coaptation element, with a smaller cross-section proximally (towards the atrium) and larger cross-section distally (towards the ventricle), would be attached to a rigid distal railing and anchor. During systolic contraction, the anchor and therefore the attached coaptation element would move towards the annulus, thus allowing the tricuspid leaflets to coapt around the larger cross-section of the device. Conversely, diastolic expansion of the RV would bring the anchor and therefore the coaptation element downwards such that the smaller cross-section of the device is now within the annulus plane, thus minimizing diastolic stenosis. A combination of a tapered element with a spring could be used if RV wall motion towards the annulus is not sufficient to move the device.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A system for delivering a coaptation member to a position within native tricuspid heart valve leaflets to reduce regurgitation therethrough, comprising:

a ventricular anchor on a distal end of a flexible rail having a length sufficient to extend from outside a body through the subclavian vein and past the native tricuspid annulus into the right ventricle, the ventricular anchor configured to be anchored within the right ventricle;

a coaptation member on a distal end of a delivery catheter configured to be advanced from outside the body over the flexible rail until the coaptation member is positioned within the native tricuspid heart valve leaflets, wherein the coaptation member comprises a plurality of elongated members in contact with one another along their lengths and held together at opposite ends, the elongated members being capable of repositioning with respect to one another from external forces;

wherein the position of the coaptation member is adjustable along the flexible rail; and a locking collet carried by the catheter for locking the position of the delivery catheter relative to the flexible rail by clamping onto the flexible rail, the locking collet being sized to enable it to be subcutaneously secured immediately outside the subclavian vein.

2. The system of claim 1, wherein the locking collet includes two internally threaded tubular grips each attached to separate sections of the delivery catheter and engaging a common externally threaded tubular shaft member through which the flexible rail passes, and a tubular wedge member interposed between the tubular shaft member and the flexible rail, wherein clamping the locking collet onto the flexible rail comprises screwing the tubular grips toward each other over the tubular shaft member to cam the wedge member inward.

3. The system of claim 1, wherein the plurality of elongated members are covered with a sleeve of pericardium or biocompatible material.

4. The system of claim 1, wherein the plurality of elongated members comprise thin balloons that are individually inflatable and deflatable.

5. The system of claim 4, further including an inflation medium for the plurality of elongated members that is fluid at time of inflation and cures into a solid or semi-solid over time.

6. The system of claim 1, wherein the plurality of elongated members comprise tubes.

7. The system of claim 1, wherein the elongated members are configured to be added or deleted as needed to reduce regurgitation through the tricuspid valve.

8. A system for delivering a coaptation member to a position within native tricuspid heart valve leaflets to reduce regurgitation therethrough, comprising:
 a ventricular anchor on a distal end of a flexible rail having a length sufficient to extend from outside a body through the subclavian vein and past the native tricuspid annulus into the right ventricle, the ventricular anchor configured to be anchored within the right ventricle;
 a first catheter having a balloon thereon configured to be advanced from outside the body over the flexible rail until the balloon is positioned substantially within the tricuspid heart valve leaflets, the balloon on the first catheter being inflatable to center the flexible rail within the tricuspid annulus;
 a coaptation member on a second catheter advanceable over the flexible rail until the coaptation member is positioned within the native tricuspid heart valve leaflets, wherein the second catheter includes a pair of relatively flexible regions directly proximal and distal to the coaptation member and a distal section of the second catheter is adapted to lock down on the flexible rail, wherein a position of the coaptation member within the tricuspid annulus may be adjusted by advancing and compressing the second catheter to cause the two flexible regions to buckle and displace the coaptation member laterally with respect to an axis of the second catheter;
 wherein the position of the coaptation member is adjustable along the flexible rail; and
 a lock carried by the second catheter for locking the position of the second catheter relative to the flexible rail by clamping the lock onto the flexible rail.

9. The system of claim 8, wherein a spring is provided on the flexible rail between the coaptation member and the ventricular anchor so that the coaptation member can move axially with respect to the tricuspid annulus from compression and expansion of the spring.

10. The system of claim 8, wherein the ventricular anchor comprises a pair of concentric corkscrew anchors, one having a clockwise orientation and the other having a counterclockwise orientation.

11. The system of claim 8, wherein the coaptation member comprises a frame formed from a plurality of struts that supports a bell-shaped tissue cover formed by one or more panels of bioprosthetic tissue or flexible polymer sewn around the struts of the frame, the coaptation member being open toward the right ventricle and closed toward the right atrium.

12. The system of claim 8, further including a pair of pull wires extending through the second catheter for altering the position of the coapting member within the tricuspid valve leaflets, wherein the position of the coaptation member within the tricuspid annulus is adjustable by pulling one of the pull wires in conjunction with rotating the second catheter.

13. The system of claim 12, wherein the pull wires are connected to the coaptation member for angular adjustment of the coaptation member at the flexible region directly proximal to the coaptation member.

14. A system for delivering a coaptation member to a position within native tricuspid heart valve leaflets to reduce regurgitation therethrough, comprising:
 a ventricular anchor on a distal end of a flexible rail having a length sufficient to extend from outside a body through the subclavian vein and past the native tricuspid annulus into the right ventricle, the ventricular anchor configured to be anchored within the right ventricle;
 a coaptation member on a distal end of a delivery catheter configured to be advanced from outside the body over the flexible rail until the coaptation member is positioned within the native tricuspid heart valve leaflets, wherein the coaptation member comprises a plurality of elongated members of circular cross-section in contact with one another along their lengths and held together at opposite ends, the elongated members being capable of repositioning with respect to one another from external forces;
 a secondary anchor for the coaptation member configured to attach within a blood passageway opening to the right atrium, and the delivery catheter connects via a sliding mechanism and a rod to the secondary anchor, wherein the sliding mechanism and rod permit adjustment of the relative positions of the secondary anchor and the coaptation member;
 wherein the position of the coaptation member is adjustable along the flexible rail; and
 a lock configured to lock the position of the delivery catheter relative to the flexible rail.

15. The system of claim 14, wherein the sliding mechanism comprises an adjustable sleeve on the delivery catheter.

16. The system of claim 14, wherein the secondary anchor and rod are adapted to reach and anchor within the superior vena cava.

17. The system of claim 14, wherein the secondary anchor comprises two stent structures, one adapted to be expanded in the superior vena cava and the other in the inferior vena cava, and the coaptation member connects via the rod and sliding mechanism to a connecting wire or rod extending between the two stent structures.

18. The system of claim 14, wherein the plurality of elongated members are covered with a sleeve of pericardium or biocompatible material.

* * * * *